United States Patent
Kauvar et al.

(10) Patent No.: US 10,654,915 B2
(45) Date of Patent: May 19, 2020

(54) ANTIBODIES USEFUL IN PASSIVE INFLUENZA IMMUNIZATION

(71) Applicant: Trellis Bioscience, LLC, South San Francisco, CA (US)

(72) Inventors: Lawrence M. Kauvar, San Francisco, CA (US); Stote Ellsworth, Palo Alto, CA (US); William Usinger, Lafayette, CA (US); Krista Maureen McCutcheon, Burlingame, CA (US); Minha Park, Brisbane, CA (US)

(73) Assignee: TRELLIS BIOSCIENCE, LLC, Redwood City, CA (US)

( * ) Notice: Subject to any disclaimer, the term of this patent is extended or adjusted under 35 U.S.C. 154(b) by 0 days.

(21) Appl. No.: 14/363,297

(22) PCT Filed: Dec. 5, 2012

(86) PCT No.: PCT/US2012/068037
§ 371 (c)(1),
(2) Date: Jun. 5, 2014

(87) PCT Pub. No.: WO2013/086052
PCT Pub. Date: Jun. 13, 2013

(65) Prior Publication Data
US 2014/0322210 A1    Oct. 30, 2014

Related U.S. Application Data

(60) Provisional application No. 61/567,046, filed on Dec. 5, 2011.

(51) Int. Cl.
*C07K 16/10* (2006.01)
*A61K 39/00* (2006.01)

(52) U.S. Cl.
CPC .... *C07K 16/1018* (2013.01); *A61K 2039/505* (2013.01); *A61K 2039/507* (2013.01); *C07K 2317/21* (2013.01); *C07K 2317/31* (2013.01); *C07K 2317/33* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,625,015 A * | 11/1986 | Green et al. | 530/324 |
| 6,235,708 B1 | 5/2001 | Holloway | |
| 7,262,270 B2 | 8/2007 | Weissenhorn et al. | |
| 7,696,330 B2 | 4/2010 | Meulen et al. | |
| 8,288,090 B2 | 10/2012 | Fomsgaard | |
| 2003/0100096 A1 | 5/2003 | Holloway | |
| 2009/0203538 A1 | 8/2009 | Sugioka et al. | |
| 2009/0311183 A1 | 12/2009 | Devy et al. | |
| 2009/0311265 A1 | 12/2009 | Van Den Brink et al. | |
| 2010/0086555 A1 * | 4/2010 | Lanzavecchia | 424/159.1 |
| 2011/0319600 A1 | 12/2011 | Kuta et al. | |
| 2012/0128671 A1 | 5/2012 | Horowitz et al. | |
| 2016/0083456 A1 | 3/2016 | Wittekind | |

FOREIGN PATENT DOCUMENTS

| | | |
|---|---|---|
| RU | 2006103301 | 9/2007 |
| WO | WO2003080672 | 10/2003 |
| WO | WO -2004/080403 | 9/2004 |
| WO | 2007/134327 A2 | 11/2007 |
| WO | WO2005007697 | 1/2008 |
| WO | 2008/028946 A2 | 3/2008 |
| WO | WO2008110937 | 9/2008 |
| WO | 2009/053604 A2 | 4/2009 |
| WO | 2009/079259 A2 | 6/2009 |
| WO | 2009/121004 A2 | 10/2009 |
| WO | 2010/010466 A2 | 1/2010 |
| WO | 2010/010467 A2 | 1/2010 |
| WO | WO -2011/160083 | 1/2010 |
| WO | 2010/022120 A1 | 2/2010 |
| WO | WO -2010/027818 | 3/2010 |
| WO | 2010/074656 A1 | 7/2010 |
| WO | 2010/130636 A1 | 11/2010 |
| WO | 2011/117848 A1 | 9/2011 |
| WO | WO -2011/126370 | 10/2011 |
| WO | 2012/045001 A2 | 4/2012 |
| WO | 2013/007770 A1 | 1/2013 |
| WO | 2013/114885 A1 | 8/2013 |
| WO | 2013/132007 A1 | 9/2013 |
| WO | 2014/152841 A1 | 9/2014 |

OTHER PUBLICATIONS

Usinger et al. (Abstract, Jul. 16-20, 2011, American Society of Virology in IDS on Mar. 22, 2016).*

(Continued)

*Primary Examiner* — Agnieszka Boesen
(74) *Attorney, Agent, or Firm* — MH2 Technology Law Group, LLP

(57) ABSTRACT

Specific monoclonal antibodies and fragments including bispecific antibodies thereof that are crossreactive with multiple clades of influenza virus including both Group 1 and Group 2 representatives are disclosed. These antibodies are useful in controlling influenza epidemics and pandemics as well as in providing prophylactic or therapeutic protection against seasonal influenza.

15 Claims, 5 Drawing Sheets
Specification includes a Sequence Listing.

(56) References Cited

OTHER PUBLICATIONS

Schoofs et al. (Journal of Immunology, 1988, vol. 140 p. 611-616).*
Mottet et al. (Journal of Virology, 1999, vol. 80, p. 2977-2986).*
Bianchi et al., "Universal influenza B vaccine based on the maturational cleavage site of the hemagglutinin precursor," J Virol (2005) 79(12):7380-7388.
Corti et al., "A neutralizing antibody selected from plasma cells that binds to group 1 and group 2 influenza A hemagglutinins," Science (2011) 333(6044):850-856.
Dreyfus et al., "Highly conserved protective epitopes on influenza B viruses," Science (2012) 337(6100):1343-1348.
Ekiert et al., "A highly conserved neutralizing epitope on group 2 influenza a viruses," Science (2011) 333(6044):843-850.
Grandea et al., "Human antibodies reveal a protective epitope that is highly conserved among human and nonhuman influenza A viruses," Proc Natl Acad Sci USA (2010) 107(28):12658-12663.
International Preliminary Report on Patentability and Written Opinion for PCT/US2012/068037, dated Jun. 10, 2014, 8 pages.
International Search Report for PCT/US2012/068037, dated Jun. 12, 2013, 6 pages.
Sui et al., "Structural and functional bases for broad-spectrum neutralization of avian and human influenza A viruses," Nat Struct Mol Biol (2009) 16(3):265-273.
Throsby et al., "Heterosubtypic neutralizing monoclonal antibodies cross-protective against H5N1 and H1N1 recovered from human IgM+ memory B cells," PLoS One (2008) 3(12):e3942.
Yoshida et al., "Cross-protective potential of a novel monoclonal antibody directed against antigenic site B of the hemagglutinin of influenza A viruses," PLoS Pathog (2009) 5(3):e1000350.
Bright; et al., "Cross-clade protective immune responses to influenza viruses with H5N1 HA and NA elicited by an influenza virus-like particle", PLoS One (Jan. 30, 2008), 3(1):e1501.
Donis et al., "Distinct Lineages of Influenza Virus H4 Hemagglutinin Genes in Different ReQions of the World", Virology (1989) 169:408-417.
Doyle; et al., "A monoclonal antibody targeting a highly conserved epitope in influenza B neuraminidase provides protection against drug resistant strains", Biochemical and Biophysical Research Communications (Nov. 2013), 441(1):226-229.
Ekiert et al., "Antibody Recognition of a Highly Conserved Influenza Virus Epitope", Science (2009) 324:246-251.
European Search Report dated Aug. 7, 2015, by the European Patent Office for European Patent Application No. 12854682.7, 8 pages.
International Search Report and Written Opinion dated Aug. 11, 2015, from the European Patent Office, for International Patent Application No. PCT/US2015/014521 (filed Feb. 4, 2015), 17 pages.
International Search Report and Written Opinion dated Jun. 12, 2013, from the International Searching Authority, for International Patent Application No. PCT/US12/68037 (filed Dec. 5, 2012), 14 pages.
International Search Report and Written Opinion dated Nov. 25, 2011, from the International Searching Authority, for International Patent Application No. PCT/US11/40982 (filed 17 Jun. 2011), 11 pages.
International Search Report and Written Opinion dated Aug. 28, 2014, from the International Searching Authority, for International Patent Application No. PCT/US14/27939 (filed Mar. 14, 2014), 14 pages.
Kostolansky et al., "Antibody Response to Hidden Epitope of Influenza A Haemagglutinin Elicited by Anti-Idiotypic Antibodies", Acta vifologica (1994) 38:215-222.
Kuboto-Koketsu; et al., "Broad neutralizing human monoclonal antibodies against influenza virus from vaccinated healthy donors", Biochem Biophys Res Commun (Sep. 11, 2009), 387(1):180-5.
McCutcheon; et al., "Multiplexed screening of natural humoral immunity identifies antibodies at fine specificity for complex and dynamic viral targets", MABS (Jan. 8, 2014), 6(2):460-473.
Prabhu et al., "Monoclonal Antibodies against the Fusion Peptide of Hemagglutinin Protect Mice from Lethal Influenza A Virus H5N1 Infection", Journal of Virology (2009) 83(6):2553-2562.
Steel; et al., "Influenza virus vaccine based on the conserved hemagglutinin stalk domain", Mbio (Apr. 2010), 1(1):1-9.
Sui; et al., "Wide Prevalence of Heterosubtypic Broadly Neutralizing Human Anti-Influenza A Antibodies", Clinical Infectious Diseases (Apr. 15, 2011), 52(8):1003-1009.
Supplementary European Search Report for EP 11796555.8, dated Oct. 22, 2013, 17 pages.
Usinger; et al., "Human monoclonal antibody 53 shows unique cross-clade neutralization of influenza", American Society of Virology (Jul. 16-20, 2011), Abstract only.
Wagner; et al., "Bispecific antibody generated with sortase and click chemistry has broad antiinfluenza virus activity", Proceedings of the National Academy of Sciences (Nov. 10, 2014), 111(47):16820-16825.
Wang; et al., "Broadly Protective Monoclonal Antibodies against H3 Influenz Viruses following Sequential Immunization with Different Hemagglutinins", PLoS (Feb. 2010), 6(2):e1000796.
Yasugi; et al., "Human monoclonal antibodies broadly neutralizing against influenza B virus", PLoS Pathogens (Feb. 2013), 9(2):1-12.
Zanin; et al., "An Anti-H5N1 Influenza Virus FcDart Antibody is a Highly Efficacious Therapeutic Agent and Prophylactic against H5N1 Influenza Virus Infection", Journal of Virology (Feb. 11, 2015), 89(8):4549-4561.
Ziegler et al., "Type- and Subtype-Specific Detection of influenza Viruses in Clinical Specimens by Rapid Culture Assay", Journal of Clinical Microbiology (1995) 33(2):318-321.
Abrahamson, M. et al. "Identification of the Probable Inhibitory Reactive Sites of the Cysteine Proteinase Inhibitors Human Cystatin C and Chicken Cystatin." The Journal of Biological Chemistry, 1987, vol. 262, No. 20, pp. 9688-9694.
Carragher et al. "A Novel Role for Non-Neutralizing Antibodies against Nucleoprotein in Facilitating Resistance to Influenza Virus." J Immunol 2008; 181 :4168-4176.
Krause et al. A Broadly Neutralizing Human Monoclonal Antibody That Recognizes a Conserved, Novel Epitope on the Globular Head of the Influenza Hint Virus Hemagglutinin. Journal of Virology, vol. 85, No. 20, Oct. 15, 2011 (Oct. 15, 2011), pp. 10905-10908, XP055044176, ISSN: 0022-538X DOI: 10.1128/JVL00700-11.
Rudikoff et al. "Single amino acid substitution altering antigen-binding specificity." PNAS, vol. 79, p. 1979-83, Mar. 1982 (Mar. 1982).
Song, G. et al. "Progesterone and Interferon Regulate Cystatin C in the Endometrium." Endocrinology, 2006, vol. 147, pp. 3478-3483.
Tamura et al. "Structural Correlates of an Anticarcinoma Antibody: Identification of Specificity-Determining Residues (SDRs) and Development of a Minimally Immunogenic Antibody Variant by Retention of SDRs Only." J Immunol., vol. 164, p. 1432-41, Feb. 2000 (Feb. 2000).
Wang Taia T. et al. "Broadly protective monoclonal antibodies against H3 influenza viruses following sequential immunization with different hemagglutinins", PLoS Pathogens, 2010, 6(2): e1000796.
Weltzin et al. "Intranasal Antibody Prophylaxis for Protection Against Viral Disease." Clinical Microbiology Reviews, Washington, D.C., US, vol. 12, No. 3, Jul. 1, 1999 (Jul. 1, 1999). pp. 383-393.
Ye et al. "Intranasai Delivery of an IgA Monoclonal Antibody Effective against Sublethal H5N1 Influenza Virus Infection in Mice." Clinical and Vaccine Immunology, Sep. 2010, p. 1363-1370.
Canadian Office Action issued in corresponding Canadian Patent Application No. 2,861,515 dated Jul. 19, 2019, pp. 1-4.
Australian Office Action issued in Australian Patent Application No. 2012347878 dated May 2, 2017, pp. 1-3.
Canadian Office Action issued in Canada Patent Application No. 2,861,515 dated Sep. 4, 2018, pp. 1-6.
English-language translation of Chinese Office Action issued in Chinese Patent Application No. 201280067362.1 dated Aug. 27, 2015, pp. 1-5.
English-language translation of Chinese Office Action issued in Chinese Patent Application No. 201280067362.1 dated Jul. 14, 2016, pp. 1-4.

(56) References Cited

OTHER PUBLICATIONS

English-language translation of Chinese Office Action issued in Chinese Patent Application No. 201280067362.1 dated Apr. 5, 2017, pp. 1-3.
English-language translation of Chinese Office Action issued in Chinese Patent Application No. 201280067362.1 dated Jan. 4, 2018, pp. 1-2.
English-language translation of Chinese Office Action issued in Chinese Patent Application No. 201280067362.1 dated Jul. 26, 2018, pp. 1-2.
European Communication issued in European Patent Application No. 12 854 682.7 dated Jul. 14, 2016, pp. 1-5.
European Communication issued in European Patent Application No. 12 854 682.7 dated Jun. 12, 2017, pp. 1-10.
English-language translation of Israeli Office Action issued in Israeli Patent Application No. 232976 dated Mar. 1, 2017, pp. 1-4.
English-language translation of Israeli Office Action issued in Israeli Patent Application No. 232976 dated Oct. 15, 2018, pp. 1-6.
English-language translation of Indian Office Action issued in Indian Patent Application No. 5528/DELNP/2014 dated Feb. 6, 2019, pp. 1-6.
English-language translation of Japanese Office Action issued in Japanese Patent Application No. 2014-546038 dated Sep. 13, 2016, pp. 1-8.
English-language translation of Japanese Office Action issued in Japanese Patent Application No. 2014-546038 dated Sep. 5, 2017, pp. 1-7.
English-language translation of Mexican Office Action issued in Mexican Patent Application No. MX/a/2014/006786 dated Jan. 25, 2018, pp. 1-2.
English-language translation of Mexican Office Action issued in Mexican Patent Application No. MX/a/2014/006786 dated Oct. 1, 2018, pp. 1-3.
New Zealand Office Action issued in New Zealand Patent Application No. 626716 dated Mar. 10, 2015, pp. 1-3.
New Zealand Office Action issued in New Zealand Patent Application No. 626716 dated Oct. 12, 2016, pp. 1-4.
English-language translation of Russian Office Action issued in Russian Patent Application No. 2014127287 (044124) dated Aug. 8, 2016, pp. 1-3.
English-language translation of Russian Office Action issued in Russian Patent Application No. 2014127287 (044124) dated Dec. 13, 2016, pp. 1-2.
English-language translation of Russian Office Action issued in Russian Patent Application No. 2014127287 (044124) dated Jul. 24, 2017, pp. 1-3.

\* cited by examiner

ANTIBODIES USEFUL IN PASSIVE INFLUENZA IMMUNIZATION

CROSS-REFERENCE TO RELATED APPLICATIONS

This application is the national phase of PCT application PCT/US2012/068037 having an international filing date of 5 Dec. 2012, which claims benefit of U.S. provisional patent application No. 61/567,046 filed 5 Dec. 2011. The contents of the above patent applications are incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 388512012900SeqList.txt, date recorded: Jun. 5, 2014, size: 55,181 bytes).

TECHNICAL FIELD

The invention relates to the field of passive immunization against influenza. More particularly, specific antibodies that bind near to the $HA_0$ maturation cleavage site consensus sequence of influenza hemagglutinin A, including antibodies secreted by human cells are described.

BACKGROUND ART

The hemagglutinin protein (HA) of influenza virus has a globular head domain which is highly heterogeneous among flu strains and a stalk region containing a fusion site which is needed for entry into the cells. HA is present as a trimer on the viral envelope. The uncleaved form of hemagglutinin protein ($HA_0$) is activated by cleavage by trypsin into $HA_1$ and $HA_2$ portions to permit the fusion site to effect virulence. The two cleaved portions remain coupled using disulfide bonds but undergo a conformational change in the low pH environment of the host cell endosomal compartment which leads to fusion of the viral and host cell membranes.

The cleavage site contains a consensus sequence that is shared both by influenza A and influenza B and by the various strains of influenza A and B. The uncleaved hemagglutinin protein trimer ($HA_0$) is referred to as the inactivated form, whereas when cleaved into $HA_1$ and $HA_2$ portions, the hemagglutinin protein is referred to as being in the activated form.

Bianchi, E., et al., *J. Virol.* (2005) 79:7380-7388 describe a "universal" influenza B vaccine based on the consensus sequence of this cleavage site wherein a peptide comprising this site was able to raise antibodies in mice when conjugated to the outer membrane protein complex of *Neisseria meningitidis*. Monoclonal antibodies which appear to bind to the consensus sequence were also described. In addition, successful passive transfer of antiserum was observed in mice. Other prior art vaccines, such as those described in WO2004/080403 comprising peptides derived from the M2 and/or HA proteins of influenza induce antibodies that are either of weak efficacy or are not effective across strains.

Antibodies described in the art which bind the HA stalk region involve those developed by Crucell, CR6261 and CR8020 described in Throsby, M., et al., *PLoS One* (2008) 3:e3942, Ekiert, D. C., et al., *Science* (2011) 333:843-850, and Sui, J., et al., *Nat. Struct. Mol. Biol.* (2009) 16:265-273.

An MAB has also been developed against the conserved M2E antigen as described by Grandea, A. G., et al., *PNAS USA* (2010) 107:12658-12663. M2E is on the surface of infected cells and is also the target of amantadine and rimantadine. Drug resistance has occurred against these antibiotics which suggests that this target does not serve an essential function.

An additional antibody has been described by the Lanzavecchia Group: Corti, D., et al., *Science* (2011) 333:850-856 which binds and neutralizes both Group 1 and Group 2 strains of influenza A, but the potency is not as high as those described herein as shown in the examples below. In addition, an MAB that is immunoreactive against both influenza A and B as described in Dreyfus, C., et al., *Science* (2012) 337:1343-1348 has less potency than those described below.

PCT application publication No. WO2011/160083, incorporated herein by reference, describes monoclonal antibodies that are derived from human cells and useful in passive vaccines. The antibodies show high affinities of binding to influenza viral clade H1, which is in Group 1, and some of the antibodies also show high affinities to H9, also in Group 1 and/or to H7 in Group 2 and/or H2 in Group 1. Some of the antibodies disclosed bind only the inactivated trimer form, presumably at the consensus cleavage region, while others are able to bind activated hemagglutinin protein which has already been cleaved.

There remains a need for antibodies that bind additional clades and show enhanced affinity thereto.

DISCLOSURE OF THE INVENTION

The invention provides monoclonal antibodies that bind trimers representative of either or both Group 1 and Group 2 of influenza A with enhanced affinity. Such antibodies are able to confer passive immunity in the event of a pandemic caused, for example, by a previously unidentified influenza strain or a strain against which protection is not conferred by the seasonal vaccines currently available. As at least some of the antibodies bind across many strains, indicative of targeting an essential site, they are likely to bind even previously unencountered strains. Such antibodies are also useful to ameliorate or prevent infection in subjects for whom vaccination failed to produce a fully protective response or who are at high risk due to a weak immune system (e.g., the very young, the elderly, transplant patients, cancer or HIV chemotherapy treated patients).

Thus, in one aspect, the invention is directed to binding moieties, notably monoclonal antibodies or immunoreactive fragments thereof that are broadly crossreactive with influenza A virus of Group 1 including H1, H2, H5, H6, H8, H9, H11, H13, H16 or Group 2 including H3 and H7 as type specimens, or that show cross-Group reactivity. Some of the antibodies illustrated below bind to an epitope contained in the $HA_0$ protein specifically and recognize the native trimeric form of HA, as well as the activated form.

Particularly important are bispecific antibodies and fragments thereof which are able to enhance the range of viral clades that can be bound specifically.

As is well understood in the art, non-immunoglobulin based proteins may have similar epitope recognition properties as antibodies and can also provide suitable embodiments, including binding agents based on fibronectin, transferrin or lipocalin. Nucleic acid based moieties, such as aptamers also have these binding properties.

In other aspects, the invention is directed to methods to use the binding moieties of the invention for passively inhibiting viral infection in subjects that are already exposed to the virus or that are already infected. The invention is also directed to recombinant materials and methods to produce antibodies or fragments.

Figure 1:
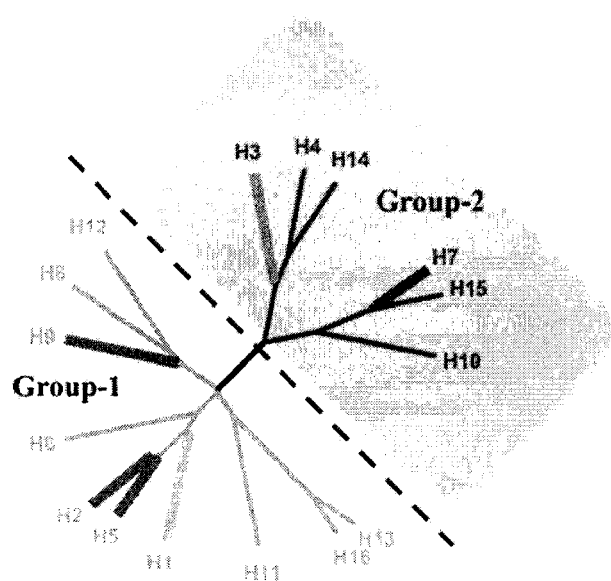
FIG. 1 shows the art-known classification of influenza virus into groups of significant clades.

| Virus/<br>subtype | Strain | Sequence[a] | |
|---|---|---|---|
| B/$HA_0$ | Consensus[b] | PAKLLKER<br>(SEQ ID<br>NO: 55) | ↓ GFFGAIAGFLE<br>(SEQ ID<br>NO: 56) |

[a]The position of cleavage between $HA_1$ and $HA_2$ is indicated by the arrow.
[b]The consensus is the same for both the Victoria and Yamagata lineages.

As indicated, strict consensus occurs starting with the arginine residue upstream of the cleavage site and thus preferred consensus sequences included in the test peptides of the invention have the sequence RGI/L/F FGAIAGFLE (SEQ ID NO:57). It may be possible to use only a portion of this sequence in the test peptides.

As noted above, once cells that secrete the desired antibodies have been identified, it is straightforward to retrieve the nucleotide sequences encoding them and to produce the desired antibodies on a large scale recombinantly. This also enables manipulation of the antibodies so that they can be produced, for example, as single-chain antibodies or in terms of their variable regions only.

The retrieved nucleic acids may be physically stored and recovered for later recombinant production and/or the sequence information as to the coding sequence for the antibody may be retrieved and stored to permit subsequent synthesis of the appropriate nucleic acids. The availability of the information contained in the coding sequences and rapid synthesis and cloning techniques along with known methods of recombinant production permits rapid production of needed antibodies in the event of a pandemic or other emergency.

For reference, the sequences of human constant regions of both heavy and light chains have been described and are set forth herein as SEQ ID NOS:1-3. In the above-referenced WO2011/160083, various monoclonal antibodies with variable regions of determined amino acid sequence and nucleotide coding sequences have been recovered that bind with varying degrees of affinity to HA protein of various strains of influenza. The structures of variable regions, both light and heavy chains, of those of particular interest herein are set forth for convenience herein as SEQ ID NOS:22-25. These antibodies include MAB8 and MAB53. MAB53 and MAB8 bind with particular affinity to H1; further, MAB53 binds tightly to H5, H7 and H9. MAB8 also binds H7 and H2. Neither of these antibodies binds strongly to H3, but MAB579 does bind H3 described herein. H7 and H3 are particularly attractive targets.

In more detail, each of these MABs binds to at least three different clades with reasonable or high affinity. MAB53 binds to $HA_0$ from the H1, H9 and H7 clades and MAB8 binds to $HA_0$ from H1, H7 clades and less strongly to and H3, as demonstrated by ELISA assay against $HA_0$ protein. The affinities are in the nanomolar range. Reactivity to native trimer of HA from all the Group 1 clades was verified using HA expressed in HEK293 cells with antibody binding measured by flow cytometry.

These results were confirmed using an alternative assay system, the biolevel interferometry based binding assay designated FortéBio® biosensor. As measured by this more accurate assay, the affinities are as follows:

MAB53/H1=60 pM, H5=6 nM, H7=70 pM, H9=30 pM; MAB8/H1=9 nM, H3=16 nM, H5=0.2 nM.

The additional specific antibodies identified in the present application, MAB383, MAB486, MAB579, MAB699, MAB700, MAB708, MAB710, MAB711 and MAB723 are represented by SEQ ID NOS:4-21 in terms of the amino acid sequences of their variable heavy chain and light chain. These antibodies bind with enhanced affinity to additional clades of influenza strains. For example, MAB579 binds with high affinity to both H3 and H7. Thus, these antibodies add to the repertoire of antibodies useful in prophylaxis and treatment of influenza.

Multiple technologies now exist for making a single antibody-like molecule that incorporates antigen specificity domains from two separate antibodies (bi-specific antibody). Thus, a single antibody with very broad strain reactivity can be constructed using the Fab domains of individual antibodies with broad reactivity to Group 1 and Group 2 respectively. Suitable technologies have been described by Macrogenics (Rockville, Md.), Micromet (Bethesda, Md.) and Merrimac (Cambridge, Mass.). (See, e.g., Orcutt K D, Ackerman M E, Cieslewicz M, Quiroz E, Slusarczyk A L, Frangioni J V, Wittrup K D. A modular IgG-scFv bispecific antibody topology, *Protein Eng Des Sel.* (2010) 23:221-228; Fitzgerald J, Lugovskoy A. Rational engineering of antibody therapeutics targeting multiple oncogene pathways. *MAbs.* (2011) 1:3(3); Baeuerle P A, Reinhardt C. Bispecific T-cell engaging antibodies for cancer therapy. *Cancer Res.* (2009) 69:4941-4944.)

Thus, it is particularly useful to provide antibodies or other binding moieties which bind to multiple types of hemagglutinin protein by constructing bispecific antibodies. Particularly useful combinations are those that combine the binding specificity of MAB53 (H1, H5, H9) with MAB579 (H3, H7).

All of the antibodies of the present invention include at least one of the binding specificities of the newly disclosed antibodies described above. These may be combined with various other antibodies, including those that were described in the above-referenced WO2011/160083 as well as other members of the new group of antibodies disclosed herein. All of the possible combinations of such binding specificities are within the scope of the present invention.

While MAB53 binds with high affinity to $HA_0$, it does not bind $HA_1$ implying binding to the complementary $HA_2$ fragment, which binding was confirmed. As MAB53 does not bind to $HA_0$ when tested by Western blot, it is assumed that the dominant epitope is at least in part conformational. It was been found that MAB8 and MAB53 bind to the same or nearby epitopes as demonstrated by their ability to compete with each other for binding to the $HA_0$ protein of the H1 clade.

All of the antibodies disclosed herein, including those previously disclosed in the above-referenced WO2011/160083 bind to the native HA trimer expressed on the surface of HA transfected cells. This was verified using an HA-encoding plasmid provided by S. Galloway and D. Steinhauer of Emory University. That is, the trimer displayed on the cell surface of the clades recognized by the various MAB's of the invention is recognized by these MAB's.

It was shown that MAB53 and MAB8 differ in that MAB8 is released from the $HA_0$ protein when the pH is lowered to 6, whereas MAB53 is not. This difference is significant as it appears predictive of neutralizing capability. In tests for the ability to neutralize H1N1 viral infection in a plaque reduction assay in MDCK target cells, low doses of MAB53 of 1-5 µg/ml neutralized infection by H1N1, by H7N3, H5N1 and H9N2. However, MAB8 does not neutralize infection by these strains. Thus, neutralizing strains may be preferentially selected by washing bound MAB or fragment at pH 6 during the primary screen, thus removing from $HA_0$ MAB's that are unlikely to remain bound as the antibody-virus complex enters the cell via the endosomal compartment and thus will be expected to have reduced ability to neutralize the virus. For example, in the CellSpot method $HA_0$ may be bound to solid support (fluorescent beads) and captured by the MAB or a mixture of MAB's, then washed at pH 6.

It was also shown that mice pretreated with graded doses of MAB53 survive challenge with otherwise lethal titers of H1N1 and H5N1 viruses with 100% protection against H1N1 challenge. The potency is comparable to a prior art antibody described by Crucell which does not show activity against Group 2 strains. Throsby, M., (supra) 3:e3942. The Crucell antibodies are heterosubtypic neutralizing monoclonal antibodies cross-protective against H5N1 and H1N1 recovered from human IgM+ memory B cells. MAB53 also provided full protection at 10 mg/kg; 90% survived at 2 mg/kg and 50% survived at 0.4 mg/kg. Where challenge by H5N1 was substituted for challenge by H1N1, for MAB53, 10 mg/kg gave 80% survival; 2 mg/kg gave 60% survival and 0.4 mg/kg gave 50% survival.

MAB53 and antibodies that bind to the same epitope under the same conditions, i.e., then remain bound when the pH is lowered to 6, are effective as passive vaccines suitable for protection of populations against epidemics and pandemics, and for prophylactic or therapeutic use against seasonal influenza for patients with a weakened immune system. Combinations of the epitope binding region of MAB53 with the high affinity binding epitopes of the antibodies of the present invention are particularly useful in constructing bispecific antibodies. This clearly permits, for example, effective binding of H7, H3 and H1 in the same antibody when MAB579 binding regions are included in the antibody. This is shown in Table 2 which provides the $IC_{50}$'s for various strains of influenza hemagglutinin protein shown by MAB579.

TABLE 2

MAB579 $IC_{50}$ values for various flu strains

| Subtype | Strain | $IC_{50}$ (ug/ml) | |
|---|---|---|---|
| H3 | A/Perth/16/2009 | 0.2 | |
| | A/Phillipines/2/82 x-79 | 0.9 | |
| | A/Udorn/307/1976 | 1.9 | |
| | A/New York/55/2004* | 1.1 | |
| | A/Wisconsin/67/2005 | 1.0 | |
| | A/HongKong/68 | 2.8 | |
| | A/SW/MN/02719 | 3.9 | |
| H4 | A/Bufflehead | 15.5 | |
| H7 | A/Canada/rv444/04 | 1.6 | |
| | A/Netherlands/219/03 | 0.6 | |
| | A/Sanderling/A106-125 | >20 | ⎫ |
| | A/Redknot/NJ/1523470/06 | >20 | ⎬ BirdViruses |
| | A/Ruddy Turnstone/A106-892 | >20 | ⎭ |
| H10 | A/Northern Shoveler | 0.8 | |

Figure 2:
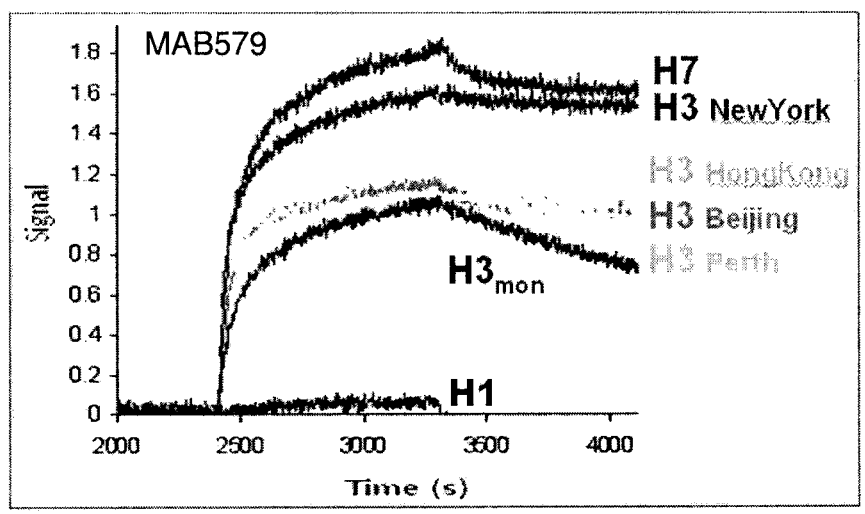
FIG. 2 shows the results of binding by MAB579 in vitro to various H7 and H3 strains, both representing Group 2.

These values were obtained in the MDCK monolayer microneutralization assay. A graphical representation of the affinity of MAB579 for various strains is also shown in FIG. 2. As shown, while H3 and H7 are tightly bound, negligible binding affinity is found for H1. Thus, it is particularly advantageous to combine the binding region of MAB579 with that of an MAB with high binding to H1. In this case, then, both Group 1 and Group 2 are represented. One embodiment of the invention includes a biospecific antibody that binds both the epitope bound by MAB53 and that bound by MAB579.

In addition to bispecific antibodies per se, the invention contemplates the use of the heavy chain only in constructs for neutralization of viral infection; such antibodies may also be bispecific. It is understood in the art that specificity is mostly conferred by the heavy chain variable regions, and in some stances, heavy chains alone have been successful as active ingredients in vaccines. Alternatively, the heavy chain of appropriate specificity may be associated with various forms of light chain to enhance the affinity or ability to neutralize virus.

It is particularly noted that the CDR3 region of the heavy chains of the antibodies described herein is extended and contains multiple tyrosine residues. It is understood that such tyrosine residues may be sulfonated as a posttranslational event. Thus, also part of the invention are vaccines which comprise the CDR3 regions of the heavy chains of MAB579, MAB699, MAB700, MAB708, MAB710, MAB711 or MAB723 wherein one or more of the tyrosine residues in said region is optionally sulfonated. These regions with or without sulfonation may also be used alone as passive vaccines. The sulfonation of the CDR3 region is consistent with criteria for sulfonation as described by Monigatti, F., et al., *Bioinformatics* (2002) 18:769-770. Other instances where CDR3 regions of heavy chains have been used successfully alone in neutralization of viral infection are described in Pejchal, R., et al., *PNAS* (2010) 107:11483-11488 and by Liu, L., et al., *J. Virol.* (2011) 85:8467-8476.

As used herein, the term "antibody" includes immunoreactive fragments of traditional antibodies even if, on occasion, "fragments" are mentioned redundantly. The antibodies, thus, include Fab fragments, $F_v$, single-chain antibodies which contain a substantially only variable regions, bispecific antibodies and their various fragmented forms that still retain immunospecificity and proteins in general that mimic the activity of "natural" antibodies by comprising amino acid sequences or modified amino acid sequences (i.e., pseudopeptides) that approximate the activity of variable regions of more traditional naturally occurring antibodies.

ANTIBODY STRUCTURES

These are presented in the following order:
1. Amino acid sequences of the constant region of human IgG1 heavy chain, human constant kappa and human constant lambda;
2. Heavy and light chain amino acid sequences of the variable regions of the heavy and light chains of MAB 383, 486, 579, 699, 700,708, 710, 711 and 723 (The CDR regions are underlined in MAB's 579, 699, 700, 708, 710, 711 and 723.);
3. Heavy and light chain variable region amino acid sequences of MAB8 and MAB53 described in WO2011/160083 (The LC sequences shown in '083 also contained constant region and this has been deleted.);
4. Nucleotide sequences encoding the constant region of human IgG1 heavy chain, human constant kappa and human constant lambda;
5. Nucleotide sequences encoding heavy and light chain amino acid sequences of the variable regions of the heavy and light chains of MAB 383, 486, 579, 699, 700,708, 710, 711 and 723;

6. Nucleotide sequences encoding heavy and light chain variable region amino acid sequences of MAB8 and MAB53.

With respect to the indicated CDR regions, it should be noted that there is more than one system for identifying CDRs. Most frequently used is the Kabat system originally set forth in Wu, T. T., et al., *J. Exp. Med.* (1970) 132:211-250. Kabat is a widely adopted system which identifies specific positions as associated with CDRs. An additional system, the Chothia numbering scheme provides slightly different results. It is described in Al-Lazikani, B., et al., *J. Molec. Biol.* (1997) 273:927-948. Depending on which system is used, slightly different results for CDRs are indicated. For example, in MAB53 the heavy chain CDR according to Kabat is KYAIN whereas the Clothia system designates GGIIRKYAIN. The heavy chain CDR2 region has an additional G at the N-terminus and the CDR3 an additional AR at the N-terminus. For the light chain, the CDR designations are identical in both systems.

Some criticism has been leveled at both systems by various workers; therefore, it is understood that the CDR regions as designated herein and in the claims may vary slightly. As long as the resulting variable regions retain their binding ability, the precise location of the CDR regions is not significant, and those regions designated in the claims are to be considered to include CDRs identified by any accepted system.

```
Human IgG1 HC amino acid sequence of
constant region
                                    (SEQ ID NO: 1)
ASTKGPSVFPLVPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human LC amino acid sequence of constant
kappa region
                                    (SEQ ID NO: 2)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Human LC amino acid sequence of constant
lambda region
                                    (SEQ ID NO: 3)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

VPAECS

MAB383 HC Amino acid sequence of variable domain
                                    (SEQ ID NO: 4)
QVQLVQSGAEVKRPGASVKVSCRASGYTFTSFGFSWVRQAPGQGLEWMGW

ISAYNGDTKSPQKLQGRVTMTTDTSTNTAYMELRSLISDDTAVYYCARAP

PLYYSSWSSDYWGQGTLLTVSS

MAB383 LC Amino acid sequence of variable domain
                                    (SEQ ID NO: 5)
DIQMTQSPGTLSLSPGERATLSCRASQSVSSNYLAWYQQKHGQAPRPLIY

GASRRATDVPDRFSGSGSGTDFTLTISRLEPEDFAVYYCQQYGSSPRTFG

QGTKLEIK

MAB486 HC Amino acid sequence of variable domain
                                    (SEQ ID NO: 6)
QVQLVESGGGMVQPGGSRRLSCAASGFSFSTYGMHWVRQAPGKGLEWVAV

ISYDGEKQYYLDSVKGRFTISRDNSKDTLYLQMNSLTAEDTAVYYCVKES

ARRLLRYFEWLLSSPFDNWGQGALVTVSS

MAB486 LC Amino acid sequence of variable domain
                                    (SEQ ID NO: 7)
DIVMTQSPDSLAVSLGERATINCKSSQTVLYTSNKKNYLAWYQQKPGQPP

KLLIYWASTRESGVPDRFSGSGSGTDFTLTISSLQAEDVAVYYCQQYYTS

PYTFGQGTKLEIK

MAB579 HC Amino acid sequence of variable domain
                                    (SEQ ID NO: 8)
QVQLVQSGAEVKKPGASVKVSCKTSGYTFTAYTIHWVRQAPGQRLEWMGW

INAGNGHTKYSQRFKGRVTITRDTSARTTYMELRSLTSEDTALYFCARGP

ETYYYDKTNWLNSHPDEYFQHWGHGTQVTVSS

MAB579 LC Amino acid sequence of variable domain
                                    (SEQ ID NO: 9)
DIQMTQSPSTLSASVGDRVTITCRASQTINNYLAWYQQKPGKAPKLLIYK

ASSLESGVPSRFSGSGSGTEFTLTISSLQPDDFATYYCQEYNNDSPLTFG

GGTKVEIK

MAB699 HC Amino acid sequence of variable domain
                                    (SEQ ID NO: 10)
QLQLVQSGAEVKKPGASVKLSCKASGYTFTSYTLHWVRQAPGQTLEWMGW

INAGNGKTKYPPKFRGRVTITRDTSATTVDMHLSSLTSEDTAVYFCARGP

ESYYYDRSDWLNSHPDEYFQYWGQGTLVIVSS

MAB699 LC Amino acid sequence of variable domain
                                    (SEQ ID NO: 11)
DIQMTQSPSTLSASVGDRVTIACRASQSISSWLAWYQQKPGKAPKLLIYK

ASQLESGVPSRFSGSGSGTEFTLTINSLQPDDFATYYCQLYNVYSPLTFG

GGTRVDIK

MAB700 HC Amino acid sequence of variable domain
                                    (SEQ ID NO: 12)
QVQLVESGADVKKPGASVTVSCKASGYTFRSFTMHWVRQVPGQRLEWMGW

INAGNGKTKYSQKFQGRVIVTRDTSASTAYMELSSLTSEDTAVYYCARGP

ETYYYDSSNWLNSHPDEYLQYWGQGTPVTVSS

MAB700 LC Amino acid sequence of variable domain
                                    (SEQ ID NO: 13)
DIVLTQSPSTLSASVGDRVTITCRASQSISSWLAWYQQKPGKAPKLLIYK

ASTLESGVPSRFSGSGSGTEFTLTISSLQPDDFATYYCQEYNNNSPLTFG

GGTKVEIK

MAB708 HC Amino acid sequence of variable domain
                                    (SEQ ID NO: 14)
QVQLVQSGADVKRPGASVTVSCKASGYTFRSFTMHWVRQVPGQRLEWMGW

INAGNGKTKYSQKFQGRVIVTRDTSANTAYMELSSLTSEDTAVYYCARGP

ETYYYDSSNWLNSHPDEYFQHWGQGTPVTVSS

MAB708 LC Amino acid sequence of variable domain
                                    (SEQ ID NO: 15)
DIQMTQSPSTLPASVGDRVTITCRASQSISSWLAWYQQKPGKAPKLLIYK
```

-continued

ASSLESGVPSRFSGSGSGTEFTLTISSLQPDDFATYYCQEYNNNSPLTFG
GGTKVEIK

MAB710 HC Amino acid sequence of variable domain
(SEQ ID NO: 16)
QVQLQESGAEVKKPGASVQVSCKASGYTFT<u>SYSVH</u>WVRQAPGQRPEWMG<u>W</u>
<u>INAGNGKTKYPQKFKG</u>RVTITRDTLARTVNIHLSSLTSEDTAVYFCAR<u>GP</u>
<u>DSYYYDRNDWLNSHPDEYFQH</u>WGQGTVVIVSS MAB710 LC Amino acid sequence of variable domain
(SEQ ID NO: 17)
DIVMTQSPSTLSASVGDRVTISC<u>RASQSIDSWLA</u>WYQQKPGKAPKLLIY<u>K</u>
<u>ASNLES</u>GVPSRFSGSGSGTEFTLTISSLQPDDFATYYC<u>QLYNVHLIT</u>FGG
GTRVDIK MAB711 HC Amino acid sequence of variable domain
(SEQ ID NO: 18)
QVQLVESGAEVKKPGASVKITCEASGYTFN<u>TYTIH</u>WLRQAPGQRLEWMG<u>W</u>
<u>INAANGHTKYSRKLRS</u>RVTIKRDTSARTSYMELSSLGSEDTAVYYCAR<u>GP</u>
<u>ETYYFDKTNWLNSHPDEYFQH</u>WGQGTLVTVSS MAB711 LC Amino acid sequence of variable domain
(SEQ ID NO: 19)
DIVMTQSPSTLSASVGDRVTITC<u>RASQSISTWLA</u>WYQQKPGKAPKLLIY<u>K</u>
<u>ASNLES</u>GVPARFSGSGSGTEFTLTISSLQPDDFATYYC<u>QEYNNDSPLIL</u>G
GGTTVEIK MAB723 HC Amino acid sequence of variable domain
(SEQ ID NO: 20)
QVQLVQSGAAVNKPGASVKVSCKASGYSFT<u>SYTLH</u>WVRQAPGQRPEWIG<u>W</u>
<u>INAGNGKVKYPRKLQG</u>RITITRDVSATTVHMELRSLTSEDTGLYYCAR<u>GP</u>
<u>ESYFFDTSNHLNSHPDEYFQF</u>WGQGTLVTVSS MAB723 LC Amino acid sequence of variable domain
(SEQ ID NO: 21)
DIQMTQSPSTLSASVGDRVTITC<u>RASQSISSYLA</u>WYQQKPGKAPKLLIY<u>K</u>
<u>ASNLES</u>GVPSRFSGSGSGTEFTLTISSLQPDDFATYYC<u>QEYNNNSPLT</u>FG
AGTKVEIK MAB8 HC amino acid sequence of variable domain
(SEQ ID NO: 22)
EVQLVESGGGLVKPGGSLRLSCAASGFTFSTYTMSWVRQAPGQGLEWVSS
ITRTSSNIYYADSVEGRFTISRDNAKNSLYLQMHSLRVEDTAVYYCARIS
GVVGPVPFDYWGQGTLITVSS MAB8 LC amino acid sequence
(SEQ ID NO: 23)
DIQMTQSPSSLSASVGDRVTITCRASQTISKYLNWYQQKPGRAPKLLIYS
ASSLQSGVPSRFTGSGSGTDFTLTISLQPEDFATYYCQQSYRPSQITFG
PGTKVDIK MAB53 HC amino acid sequence of variable domain
(SEQ ID NO: 24)
QVQLVQSGAEVRKPGSSVKVSCKVSGGIIRKYAINWVRQAPGQGLEWMGG
IIAIFNTANYAQKFQGRVTITADESTSTVYMELSSLRSEDTALYYCARGM
NYYSDYFDYWGQGSLVTVSP MAB53 LC amino acid sequence
(SEQ ID NO: 25)
EIVLTQSPGTLSLSPGERATLSCRASQSVRSNNLAWYQHKPGQAPRLLIF

GASSRATGIPDRFSGSGSGTDFTLTISRLEPEDFAVYYCQQYGSSPALTF
GGGTKVEIK

Human IgG1 HC nucleotide sequence of constant
region (introns are underlined)
(SEQ ID NO: 26)
GCCTCCACCAAGGGCCCATCAGTCTTCCCCCTGGCACCCTCTACCAAGAG
CACCTCTGGGGGCACAACGGCCCTGGGCTGCCTGGTCAAGGACTACTTCC
CCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAG
CGTGGTGACCGTGCCCTCCAGCAGCTTGGGCACCCAGACCTACATCTGCA
ACGTGAATCACAAGCCCAGCAACACCAAGGTGGACAAG<u>AGAGTTGGTGAG</u>
<u>AGGCCAGCACAGGGAGGGAGGGTGTCTGCTGGAAGCCAGGCTCAGCGCTC</u>
<u>CTGCCTGGACGCATCCCGGCTATGCAGTCCCAGTCCAGGGCAGCAAGGCA</u>
<u>GGCCCCGTCTGCCTCTTCACCCGGAGGCCTCTGCCCGCCCCACTCATGCT</u>
<u>CAGGGAGAGGGTCTTCTGGCTTTTTCCCCAGGCTCTGGGCAGGCACAGGC</u>
<u>TAGGTGCCCCTAACCCAGGCCCTGCACACAAAGGGGCAGGTGCTGGGCTC</u>
<u>AGACCTGCCAAGAGCCATATCCGGGAGGACCCTGCCCCTGACCTAAGCCC</u>
<u>ACCCCAAAGGCCAAACTCTCCACTCCCTCAGCTCGGACACCTTCTCTCCT</u>
<u>CCCAGATTCCAGTAACTCCCAATCTTCTCTCTGCAGAGCCCAAATCTTGT</u>
GACAAAACTCACACATGCCCACCGTGCCCAG<u>GTAAGCCAGCCCAGGCCTC</u>
<u>GCCCTCCAGCTCAAGGCGGGACAGGTGCCCTAGAGTAGCCTGCATCCAGG</u>
<u>GACAGGCCCCAGCCGGGTGCTGACACGTCCACCTCCATCTCTTCCTCAGC</u>
ACCTGAACTCCTGGGGGGACCGTCAGTCTTCCTCTTCCCCCCAAAACCCA
AGGACACCCTCATGATCTCCCGGACCCCTGAGGTCACATGCGTGGTGGTG
GACGTGAGCCACGAAGACCCTGAGGTCAAGTTCAACTGGTACGTGGACGG
CGTGGAGGTGCATAATGCCAAGACAAAGCCGCGGGAGGAGCAGTACAACA
GCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCC
CATCGAGAAAACCATCTCCAAAGCCAAAG<u>GTGGGACCCGTGGGGTGCGAG</u>
<u>GGCCACATGGACAGAGGCCGGCTCGGCCCACCCTCTGCCCTGAGAGTGAC</u>
<u>CGCTGTACCAACCTCTGTCCCTACAGGG</u>CAGCCCCGAGAACCACAGGTGT
ACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGA
GAGCAATGGGCAGCCGGAGAACAACTACAAGACCACGCCTCCCGTGCTGG
ACTCCGACGGCTCCTTCTTCCTCTATAGCAAGCTCACCGTGGACAAGAGC
AGGTGGCAGCAGGGGAACGTCTTCTCATGCTCCGTGATGCATGAGGCTCT
GCACAACCACTACACGCAGAAGAGCCTCTCCCTGTCCCCGGGTAAATGA Human LC nucleotide sequence of constant
kappa region
(SEQ ID NO: 27)
CGAACTGTGGCTGCACCATCTGTCTTCATCTTCCCGCCATCTGATGAGCA
GTTGAAATCTGGAACTGCTAGCGTTGTGTGCCTGCTGAATAACTTCTATC
CCAGAGAGGCCAAAGTACAGTGGAAGGTGGATAACGCCCTCCAATCGGGT
AACTCCCAGGAGAGTGTCACAGAGCAGGACAGCAAGGACAGCACCTACAG

CCTCAGCAGCACCCTGACGCTGAGCAAAGCAGACTACGAGAAACACAAAG

TCTACGCCTGCGAAGTCACCCATCAGGGCCTGAGCTCGCCCGTCACAAAG

AGCTTCAACAGGGGAGAGTGTTAG

Human LC nucleotide sequence of constant
lambda region
(SEQ ID NO: 28)
GGTCAGCCCAAGGCTGCCCCCTCTGTCACTCTGTTCCCGCCCTCTAGCGA

GGAGCTTCAAGCCAACAAGGCCACACTGGTGTGTCTCATAAGTGACTTCT

ACCCGGGAGCCGTGACAGTGGCCTGGAAGGCAGATAGCAGCCCCGTCAAG

GCGGGAGTGGAGACCACCACACCCTCCAAACAAAGCAACAACAAGTACGC

GGCCAGCAGCTATCTGAGCCTGACGCCTGAGCAGTGGAAGTCCCACAGAA

GCTACAGCTGCCAGGTCACGCATGAAGGGAGCACCGTGGAGAAGACAGTG

GTCCCTGCAGAATGCTCT

MAB383 HC Nucleotide sequence of variable domain
(SEQ ID NO: 29)
CAGGTGCAGCTGGTGCAGTCTGGAGCTGAGGTGAAGAGGCCTGGGGCCTC

AGTGAAGGTCTCCTGCAGGGCTTCTGGTTACACCTTTACTAGCTTCGGTT

TCAGCTGGGTGCGACAGGCCCCAGGACAAGGGCTTGAGTGGATGGGGTGG

ATCAGCGCTTACAATGGTGACACAAAGTCTCCACAGAAGCTCCAGGGCAG

AGTCACCATGACTACAGACACATCCACGAACACAGCCTACATGGAGCTGA

GGAGCCTCATATCTGACGACACGGCCGTGTATTATTGTGCGAGAGCCCCC

CCCCTGTATTACAGTAGCTGGTCCTCAGACTACTGGGGCCAGGGAACCCT

GCTCACCGTCTCCTCA

MAB383 LC Nucleotide sequence of variable domain
(SEQ ID NO: 30)
GATATCCAGATGACGCAGTCTCCAGGCACCCTGTCTTTGTCTCCAGGGGA

AAGAGCCACCCTCTCCTGCAGGGCCAGTCAGAGTGTCAGTAGCAACTACT

TAGCCTGGTACCAGCAGAAACATGGCCAGGCTCCCAGGCCCCTCATCTAC

GGTGCATCCAGAAGGGCCACTGACGTCCCAGACAGGTTCAGTGGCAGTGG

GTCTGGGACAGACTTCACTCTCACCATCAGCAGACTGGAACCTGAAGATT

TTGCAGTGTATTATTGTCAGCAGTATGGTAGTTCACCTCGAACTTTTGGC

CAGGGGACCAAACTGGAAATCAAAC

MAB486 HC Nucleotide sequence of variable domain
(SEQ ID NO: 31)
CAGGTGCAGCTGGTGGAGTCTGGGGGAGGCATGGTCCAGCCGGGGGGGTC

CCGGAGACTCTCCTGTGCAGCCTCTGGATTCAGCTTCAGTACCTATGGCA

TGCACTGGGTCCGCCAGGCTCCAGGCAAGGGGCTGGAGTGGGTGGCAGTT

ATTTCATATGATGGAGAAAAGCAATATTATCTAGACTCCGTGAAGGGACG

ATTCACCATCTCCAGAGACAATTCCAAGGACACCCTCTATCTGCAAATGA

ACAGTCTGACAGCTGAGGACACGGCTGTGTATTACTGTGTGAAGGAATCA

GCGCGTCGATTATTACGATATTTTGAGTGGTTATTAAGTTCGCCTTTTGA

CAACTGGGGCCAGGGAGCCCTAGTCACCGTCTCCTCA

MAB486 LC Nucleotide sequence of variable domain
(SEQ ID NO: 32)
GATATCGTGATGACCCAGTCTCCAGACTCCCTGGCTGTGTCTTTGGGCGA

GAGGGCCACCATCAACTGCAAGTCCAGCCAGACTGTTTTATACACCTCCA

ACAAGAAAAATTACTTAGCCTGGTACCAACAGAAGCCAGGGCAGCCTCCT

AAACTGCTCATTTACTGGGCATCTACCCGGGAATCCGGGGTCCCTGACCG

ATTCAGTGGCAGCGGGTCTGGGACAGATTTCACTCTCACCATCAGCAGCC

TGCAGGCTGAGGATGTGGCAGTTTATTACTGTCAGCAATATTATACGTCT

CCCTACACATTTGGCCAGGGGACCAAGCTGGAGATCAAA

MAB579 HC Nucleotide sequence of variable domain
(SEQ ID NO: 33)
CAGGTGCAGCTGGTGCAGTCTGGGGCTGAGGTGAAGAAGCCTGGGGCCTC

AGTGAAGGTTTCCTGCAAGACTTCTGGATACACCTTCACAGCCTATACTA

TACACTGGGTGCGCCAGGCCCCCGGACAAAGGCTTGAGTGGATGGGATGG

ATCAACGCTGGCAATGGTCACACGAAATATTCACAGAGGTTCAAGGGCAG

AGTCACCATTACCAGGGACACATCCGCGAGGACAACCTACATGGAGCTGC

GCAGTCTGACATCTGAGGACACGGCTCTATATTTCTGTGCGAGAGGGCCC

GAGACATATTATTATGATAAAACCAATTGGCTGAACTCCCATCCAGATGA

ATACTTCCAGCACTGGGGCCACGGCACCCAGGTCACCGTCTCCTCA

MAB579 LC Nucleotide sequence of variable domain
(SEQ ID NO: 34)
GATATCCAGATGACCCAGTCTCCTTCCACCCTGTCTGCATCTGTAGGAGA

CAGAGTCACCATCACTTGCCGGGCCAGTCAGACTATTAATAACTACTTGG

CCTGGTATCAGCAGAAACCAGGGAAAGCCCCTAAACTCCTGATCTATAAG

GCGTCTAGTTTAGAAAGTGGGGTCCCATCAAGATTCAGTGGCAGTGGGTC

TGGGACAGAATTCACTCTCACCATCAGCAGCCTGCAGCCTGATGATTTTG

CAACTTATTACTGCCAAGAATATAATAATGATTCTCCCCTAACTTTCGGC

GGAGGGACCAAAGTGGAGATCAAA

MAB699 HC Nucleotide sequence of variable domain
(SEQ ID NO: 35)
CAGGTGCAGCTGGTGCAGTCCGGGGCTGAGGTGAAGAAGCCTGGGGCCTC

AGTGAAGCTTTCCTGCAAGGCTTCTGGGTACACCTTCACTTCCTATACTC

TACATTGGGTGCGCCAGGCCCCCGGACAGACACTTGAGTGGATGGGATGG

ATCAACGCTGGCAACGGTAAAACAAAATATCCACCGAAGTTCAGGGGCAG

AGTCACCATTACCAGGGACACGTCCGCGACCACAGTCGACATGCATCTAA

GCAGCCTGACATCTGAAGACACGGCTGTGTATTTCTGTGCGAGAGGGCCC

GAAAGTTATTACTATGATAGAAGTGATTGGCTGAACTCCCATCCAGATGA

ATACTTCCAGTACTGGGGCCAGGGCACCCTGGTCATCGTCTCCTCA

MAB699 LC Nucleotide sequence of variable domain
(SEQ ID NO: 36)
GATATCGTGCTGACGCAGTCTCCTTCCACCCTGTCTGCATCTGTAGGGGA

CAGAGTCACCATCGCTTGCCGGGCCAGTCAGAGTATTAGCAGCTGGCTGG

CCTGGTATCAGCAGAAACCAGGGAAAGCCCCTAAACTCCTGATCTACAAG

GCGTCTCAGTTAGAAAGTGGGGTCCCATCAAGATTCAGCGGCAGCGGATC

TGGGACAGAGTTCACTCTCACCATCAACAGCCTGCAGCCTGATGATTTTG

CAACTTATTACTGCCAACTTTATAATGTTTATTCTCCGCTCACTTTCGGC

GGGGGGACCAGGGTGGACATCAAA

MAB700 HC Nucleotide sequence of variable domain

```
(SEQ ID NO: 37)
CAGGTGCAGCTGGTGGAGTCTGGGGCTGACGTGAAGAAGCCTGGGGCCTC

AGTGACGGTTTCCTGCAAGGCCTCAGGATACACCTTCAGGAGTTTTACTA

TGCATTGGGTGCGCCAGGTCCCCGGACAAAGGCTTGAGTGGATGGGATGG

ATCAACGCTGGCAATGGTAAAACAAAGTATTCTCAGAAGTTCCAGGGCAG

AGTCATCGTTACCAGGGACACATCCGCGAGCACAGCCTACATGGAGCTGA

GCAGCCTAACATCTGAAGCACGGCTGTTTATTACTGTGCGAGAGGGCCC

GAAACATATTACTATGATAGTAGTAATTGGCTGAATTCCCATCCAGATGA

ATATCTCCAGTACTGGGGCCAGGGCACCCCGGTCACCGTCTCCTCA

MAB700 LC Nucleotide sequence of variable domain
                                    (SEQ ID NO: 38)
GATATCCAGATGACCCAGTCTCCTTCCACCCTGTCTGCGTCTGTAGGAGA

CAGAGTCACCATCACTTGCCGGGCCAGTCAGAGTATTAGTAGCTGGTTGG

CCTGGTATCAGCAGAAACCAGGGAAAGCCCCTAAACTCCTGATCTATAAG

GCGTCTACTTTAGAAAGTGGGGTCCCATCCAGGTTCAGCGGCAGTGGATC

TGGGACAGAATTCACTCTCACCATCAGCAGCCTGCAGCCTGATGATTTTG

CAACTTATTACTGCCAAGAGTATAATAATAATTCTCCGCTCACTTTCGGC

GGAGGGACCAAGGTGGAGATCAAA

MAB708 HC Nucleotide sequence of variable domain
                                    (SEQ ID NO: 39)
CAGGTGCAGCTGGTGCAGTCTGGGGCTGACGTGAAGAGGCCTGGGGCCTC

AGTGACGGTTTCCTGCAAGGCTTCAGGATACACCTTCAGGAGCTTTACTA

TGCATTGGGTGCGCCAGGTCCCCGGACAAAGGCTGGAGTGGATGGGATGG

ATCAACGCTGGCAATGGTAAAACAAAATATTCCCAGAAGTTTCAGGGCAG

AGTCATCGTTACCAGGGACACATCCGCGAACACGGCCTACATGGAGCTGA

GCAGCCTGACATCTGAAGACACGGCTGTTTATTACTGTGCGAGAGGGCCC

GAAACATATTATTATGATAGTAGTAATTGGCTGAACTCCCATCCAGATGA

ATATTTCCAGCACTGG

MAB708 LC Nucleotide sequence of variable domain
                                    (SEQ ID NO: 40)
GATATCCAGATGACCCAGTCTCCTTCCACCCTGCCTGCGTCTGTAGGAGA

CAGAGTCACCATCACTTGCCGGGCCAGTCAGAGTATTAGTAGCTGGTTGG

CCTGGTATCAGCAGAAACCAGGGAAAGCCCCTAAACTTCTGATCTATAAG

GCGTCTAGTTTAGAAAGTGGGGTCCCATCCAGGTTCAGCGGCAGTGGATC

TGGGACAGAATTCACTCTCACCATCAGCAGCCTGCAGCCTGATGATTTTG

CAACTTATTACTGCCAGGAGTATAATAATAATTCTCCGCTCACTTTCGGC

GGAGGGACCAAGGTGGAGATCAAA

MAB710 HC Nucleotide sequence of variable domain
                                    (SEQ ID NO: 41)
CAAGTGCAGCTGCAGGAGTCGGGGCTGAGGTGAAGAAGCCTGGGGCCTC

AGTGCAGGTTCCTGCAAGGCTTCTGGGTACACCTTCACGTCCTATAGCG

TACATTGGGTGCGCCAGGCCCCCGGACAAAGGCCTGAGTGGATGGGATGG

ATCAACGCTGGCAACGGAAAGACAAAATATCCACAGAAGTTCAAGGGCAG

AGTCACCATAACCAGAGACACATTAGCGCGCACTGTCAACATACATCTAA

GCAGCCTGACATCCGAAGACACGGCTGTGTATTTCTGTGCGAGAGGGCCC

GATAGTTATTACTATGATAGAAATGATTGGCTGAACTCCCATCCAGATGA

ATACTTCCAGCACTGGGGCCAGGGCACCGTGGTCATCGTCTCCTCA

MAB710 LC Nucleotide sequence of variable domain
                                    (SEQ ID NO: 42)
GATATCGTGATGACCCAGTCTCCTTCCACCCTGTCTGCATCTGTGGGAGA

CAGAGTCACCATCTCTTGCCGGGCCAGTCAGAGTATTGACAGTTGGTTGG

CCTGGTATCAGCAGAAACCAGGGAAAGCCCCTAAACTCCTGATCTATAAG

GCGTCTAATTTAGAAAGTGGGGTCCCATCAAGATTCAGCGGCAGCGGATC

TGGGACAGAATTCACTCTCACCATCAGCAGCCTGCAGCCTGATGATTTTG

CGACTTATTACTGCCAACTCTATAATGTTCATTTGATCACTTTCGGCGGA

GGGACCAGGGTGGACATCAAA

MAB711 HC Nucleotide sequence of variable domain
                                    (SEQ ID NO: 43)
CAGGTGCAGCTGGTGGAGTCTGGGGCTGAGGTGAAGAAGCCTGGGGCCTC

AGTGAAGATCACCTGCGAGGCTTCTGGATACACTTTCAATACCTATACTA

TACATTGGCTGCGCCAGGCCCCCGGACAAAGACTTGAGTGGATGGGGTGG

ATCAACGCTGCCAATGGTCATACAAAATATTCACGGAAGCTCAGGTCCAG

AGTCACCATTAAGAGGGACACATCCGCGAGGACAAGTTACATGGAGCTGA

GCAGCCTGGGATCTGAAGACACGGCTGTCTATTACTGTGCGAGAGGGCCC

GAAACATATTACTTTGATAAGACGAATTGGCTGAACTCCCATCCAGATGA

ATACTTCCAGCACTGGGGCCAGGGCACCCTGGTCACCGTCTCCTCA

MAB711 LC Nucleotide sequence of variable domain
                                    (SEQ ID NO: 44)
GATATCGTGATGACGCAGTCTCCTTCCACCCTGTCTGCATCTGTAGGAGA

CAGAGTCACCATCACTTGCCGGGCCAGTCAGAGTATTTCTACCTGGTTGG

CCTGGTATCAGCAGAAACCAGGGAAAGCCCCTAAGCTCCTGATCTATAAG

GCGTCCAATTTAGAAAGTGGGGTCCCAGCAAGATTCAGCGGCAGTGGATC

TGGGACAGAGTTCACTCTCACCATCAGCAGCCTGCAGCCTGATGATTTTG

CAACTTATTACTGCCAAGAATATAATAATGATTCTCCGCTGATTTTAGGC

GGAGGGACCACGGTGGAGATCAAA

MAB723 HC Nucleotide sequence of variable domain
                                    (SEQ ID NO: 45)
CAGGTGCAGCTGGTGCAGTCTGGGGCTGCGGTGAACAAGCCTGGGGCCTC

AGTGAAGGTTTCCTGCAAGGCTTCTGGATACAGCTTCACTAGTTACACTT

TGCATTGGGTGCGCCAGGCCCCCGGACAAAGGCCTGAGTGGATAGGGTGG

ATCAACGCTGGCAATGGTAAAGTAAAATATCCACGGAAGTTGCAGGGCAG

AATCACCATAACCAGGACGTATCCGCTACGACAGTTCACATGAACTGA

GGAGCCTGACATCTGAGGACACGGGTCTATATTACTGTGCGAGAGGGCCC

GAAAGTTACTTCTTTGATACTTCTAATCATCTGAACTCCCATCCAGATGA

ATACTTCCAGTTCTGGGGCCAGGGCACCCTGGTCACCGTCTCCTCA

MAB723 LC Nucleotide sequence of variable domain
                                    (SEQ ID NO: 46)
GATATCGTGCTGACGCAGTCTCCTTCCACCCTGTCTGCATCTGTAGGAGA

CAGAGTCACCATCACTTGCCGGGCCAGTCAGAGTATTAGTAGTTACTTGG

CCTGGTATCAACAGAAACCAGGGAAAGCCCCTAAACTCCTGATCTATAAG

GCGTCTAATTTAGAAAGTGGGGTCCCATCAAGATTCAGCGGCAGTGGATC
```

-continued

TGGGACAGAATTCACTCTCACCATCAGCAGCCTGCAGCCTGATGATTTTG

CAACTTATTATTGCCAAGAATATAATAATAACTCTCCGCTCACTTTCGGC

GCAGGGACCAAGGTGGAGATCAAA

MAB8 HC variable domain nucleotide sequence
(SEQ ID NO: 47)
GAGGTGCAGCTGGTGGAGTCTGGGGGAGGCCTGGTCAAGCCTGGGGGGTC

CCTGAGACTCTCCTGTGCAGCCTCTGGTTTCACTTTCAGTACCTATACTA

TGAGTTGGGTCCGCCAGGCTCCAGGGCAGGGGCTAGAGTGGGTCTCGTCC

ATTACTAGGACTAGTAGTAATATATACTACGCAGACTCAGTGGAGGGCCG

ATTCACCATCTCCAGAGACAACGCCAAGAACTCACTGTATCTGCAGATGC

ATAGCCTGAGAGTCGAAGACACGGCTGTGTATTACTGTGCGAGAATCAGC

GGGGTAGTGGGACCTGTCCCCTTTGACTACTGGGGCCAGGGAACCCTGAT

CACCGTCTCCTCT

MAB8 LC variable domain nucleotide sequence
(SEQ ID NO: 48)
GACATCCAGATGACCCAGTCTCCATCTTCCCTGTCTGCATCTGTAGGAGA

CAGAGTCACCATCACTTGCCGGGCAAGTCAGACCATTAGCAAGTATTTAA

ATTGGTATCAGCAGAAGCCAGGGAGAGCCCCTAAACTCCTGATCTACTCT

GCGTCCAGTTTGCAAAGTGGGGTCCCATCAAGGTTCACTGGCAGTGGATC

TGGGACAGATTTCACTCTCACCATCACCAGTCTGCAACCTGAAGATTTTG

CAACTTACTACTGTCAACAGAGTTACAGACCCTCCCAGATCACTTTCGGC

CCTGGGACCAAAGTGGATATCAAA

MAB53 HC variable domain nucleotide sequence
(SEQ ID NO: 49)
CAGGTGCAGCTGGTGCAGTCTGGGGCTGAGGTGAGGAAGCCGGGGTCCTC

GGTGAAGGTCTCCTGCAAGGTTTCTGGAGGCATCATTAGGAAATATGCTA

TCAACTGGGTGCGACAGGCCCCCGGACAAGGGCTTGAGTGGATGGGAGGG

ATCATCGCTATCTTTAATACAGCAAACTATGCACAGAAATTCCAGGGCAG

AGTCACGATTACCGCGGACGAGTCCACGAGCACAGTCTACATGGAGCTGA

GCAGCCTGAGATCTGAAGACACGGCCCTTTATTACTGTGCGAGAGGAATG

AATTACTACAGTGACTACTTTGACTACTGGGGCCAGGGAAGCCTTGTCAC

CGTCTCCCCA

MAB53 LC variable domain nucleotide sequence
(SEQ ID NO: 50)
GAAATTGTGTTGACACAGTCTCCAGGCACCCTGTCTTTGTCTCCAGGGGA

AAGAGCCACCCTCTCCTGCAGGGCCAGTCAGAGTGTTAGAAGCAACAACT

TAGCCTGGTACCAGCACAAACCTGGCCAGGCTCCCAGGCTCCTCATCTTT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTATATTACTGTCAGCAGTATGGTAGCTCACCTGCGCTCACTTTC

GGCGGAGGGACCAAGGTGGAGATCAAA

The following examples are offered to illustrate but not to limit the invention.

EXAMPLE 1

Affinity of MAB53 and MAB579

Figure 3A:
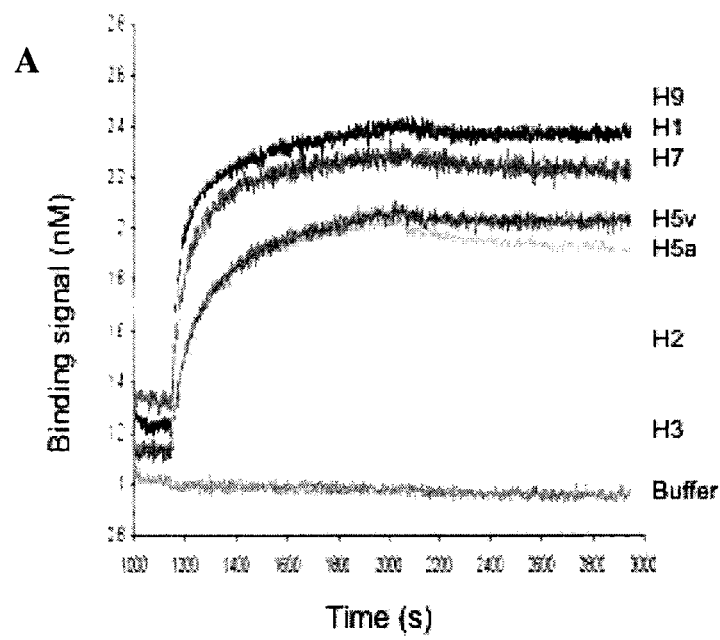
FIGS. 3A and 3B show two lead mAbs, MAB53 (Group 1) and MAB579 (Group 2) have sub-nM affinity across clades spanning the TABLE 1-continued Consensus sequence of the solvent-exposed
region of the influenza A and B
virus maturational cleavage sites
Figure 3B:
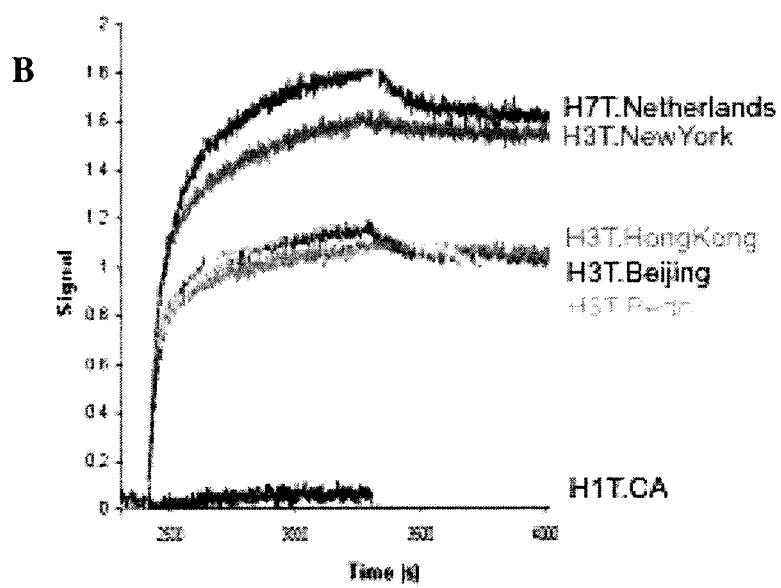

The affinity of MAB53 was reported in the above cited PCT publication. This antibody binds HA strongly from clades H5, H7, H1 and H9, with less affinity for H2 and H3. MAB579 binds HA with high affinity with respect to H7 and H3. FIGS. 3A and 3B show typical results using the standard FortéBio™ assay for each antibody.

EXAMPLE 2

Neutralization of Infection by MAB486 and MAB579

Figure 4A:
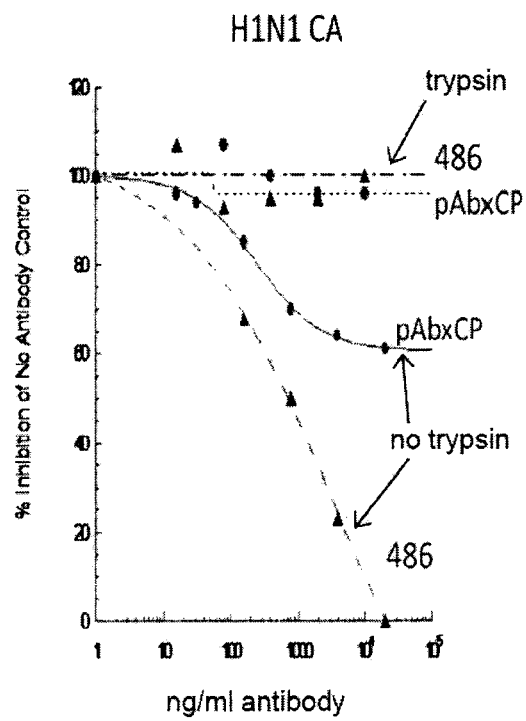
Figure 4B:
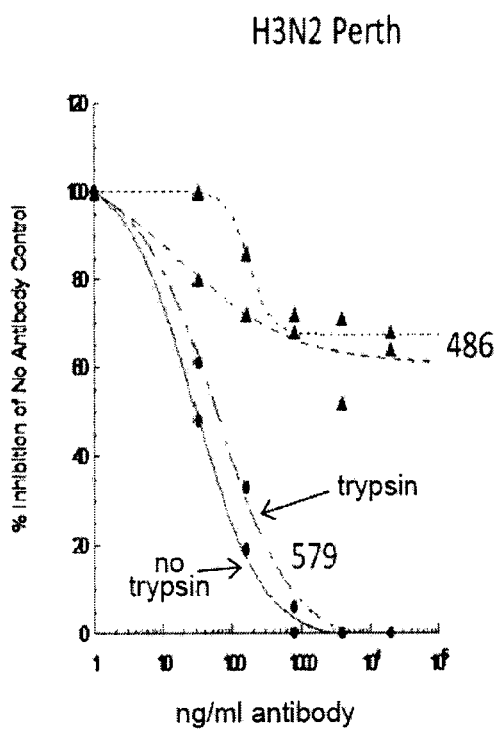

MAB's 486 and 579 were tested for inhibition of infection by H1N1 and H3N2 (A/Perth/16/2009) and plaque formation in MDCK cell monolayers in the presence or absence of trypsin in the initial infection phase. MAB486 and pAb xCP (a rabbit polyclonal raised against the cleavage site consensus sequence) neutralize H1N1 (A/California/04/2009) only in the absence of trypsin as shown in FIG. 4A, and are unable to inhibit infection and plaque formation if the virus is first activated with trypsin. This shows that antibodies directed to the fusion region with epitopes relying on intact fusion peptide (i.e., protease susceptible) are not as effective in controlling viral infection. As shown in FIG. 4B, MAB579 inhibits infection in both the presence and absence of trypsin.

The ability of MAB53 to neutralize infection was previously reported, but a comparison of the affinities and $EC_{50}$ for in vitro neutralization are compared to those for the Crucell monoclonal antibodies CR6261 in Table 3 below.

TABLE 3

Potency in vitro of Trellis mAbs vs. mAbs cloned from Crucell patents

| Strain | | MAB53 $K_D$ (nM) | MAB53 $EC_{50}$ (µg/mL) | "CR6261" $EC_{50}$ (µg/mL) | Potency Difference |
|---|---|---|---|---|---|
| H1N1 | A/CA/07/09 | 0.1 | 0.14 | 4.0 | 30x |
| H5N1 | A/VN/1204 | 0.5 | 0.10 | 3.7 | 40x |
| H2N2 | A/Mallard/MN/2008 | nd | 1.20 | nd | |
| H9N2 | Mallard/MN/98 | nd | 0.10 | nd | |

| Strain | | MAB579 KD (nM) | MAB579 $EC_{50}$ (µg/mL) | "CR8020" $EC_{50}$ (µg/mL) | Potency Difference |
|---|---|---|---|---|---|
| H3N2 | A/Wisconsin/67/2005 | nd | 1.0 | 3.5 | 3x |
| H3N2 | A/Perth/16/2009 | 0.8 | 0.05 | 2.0 | 40x |
| H3N2 | A/New York/55/2004 | 0.2 | 2.0 | 10.0 | 5x |

TABLE 3-continued

Potency in vitro of Trellis mAbs vs. mAbs cloned from Crucell patents

| H3N2 | A/Hong Kong/8/68 | 0.2 | 2.0 | 7.6 | 3x |
| H7N7 | A/Netherlands/219/03 | 0.4 | 0.7 | 13.1 | 20x |
| H7N3 | A/Canada/rv444/04 | 0.6 | 0.5 | nd | |
| H4N4 | A/Bufflehead | nd | 15.0 | >40 | 3x |
| H10N7 | A/Northern Shoveler | nd | 0.8 | nd | |

The values for $EC_{50}$ were obtained as described above.

EXAMPLE 3

Determination of Epitopes

Pepscan CLIPS™ Technology was used to map the binding sites of MAB53 and MAB579. About 6,000 unique peptides of varying lengths and with varying length connecters to constrain the ends of each peptide to mimic native structure were synthesized for H1 and for H3. Binding to the stalk region by MAB53 and MAB579 was confirmed using rabbit sera to globular head or stalk as competitors and by direct binding to peptides from the stalk region. As noted above, MAB486 binds both Group 1 and Group 2 but only in the preactivated state before protease cleavage of $HA_0$ to disulfide linked $HA_1$ and $HA_2$. It was concluded that the epitope for cross-clade binding is a discontinuous epitope spanning two monomers of the native trimeric $HA_0$.

EXAMPLE 4

In Vivo Potency (MAB53) and Pharmacokinetics (MAB53 and MAB579)

The strains used in these experiments were:
H1N1: A/CA/04/09;
H5N1: A/Vietnam/1203/04/HPAI;
H3N2: A/Perth/16/09;
H7N3: A/Red Knot/NJ/1523470/06.

To test prophylaxis, MAB53 was provided to mice as a single intraperitoneal dose of 10 mg/kg at Day −1 which was followed at Day 0 by a dose of virus 10 times the $LD_{50}$ delivered intranasally. The potency of MAB53 was determined to exhibit $EC_{50}$ at 0.4 mg/kg as compared to the Crucell antibody CR6261 which is reported to exhibit an $EC_{50}$ of 1-1.5 mg/kg (Koudstaal, W., et al., *J. Infect. Dis.* (2009) 200:1870-1873).

To test therapeutic effectiveness, MAB was given as a single intraperitoneal dose of 10 mg/kg at Day +3 for most strains or at Day +1 for H7N3. MAB53 was fully effective with respect to H1N1 and H5N1 whereas essentially all control mice were dead by Day 10. MAB579 was essentially fully effective against H3N2 and H7N3 whereas virtually all control mice were dead before Day 10.

Weight loss was also measured and declines were no worse than 20% in the treated mice.

In comparison to treatment with Tamiflu® (oseltamivir phosphate), mice (10 per group) were anesthetized and infected intranasally with 10 times the $LD_{50}$ dose of virus (H1N1 Influenza A/Ca/04/09). MAB53 (or control isotype-matched human IgG) was given i.p. at Day +1 post-infection. Tamiflu® was given by oral gavage twice daily for 4 days starting on Day +1 post-infection. Both mortality and morbidity (assessed by weight loss) were far more severe for the Tamiflu® cohort compared to the MAB53 cohort.

For controls, all of the mice were dead by eight days post infection. For those treated with Tamiflu®, all but two mice were dead before eight days post infection; these two mice survived at least to Day 14. In the group treated with MAB53, eight of the ten mice survived past Day 8 to Day 14.

With respect to weight loss, the control group declined in weight to 70% of their initial weight after eight days. The declines in weight were reversed at Day 4 for the mice treated with MAB53 and the original weight was exceeded by Day 14. In the Tamiflu® treated mice, weight loss was reversed by Day 6 but only 92% of the original weight was attained by Day 14.

Pharmacokinetics were also examined in mice for MAB53 and MAB579. These show a half-life in mice of about 7-14 days corresponding to a half-life in humans of 3-4 weeks. This corresponds to that typical for an IgG1 κ MAB. The bispecific antibody MAB579/53Bi (see Example 5) shows a similar half-life.

EXAMPLE 5

Construction of MAB579/53Bi

Figure 5:
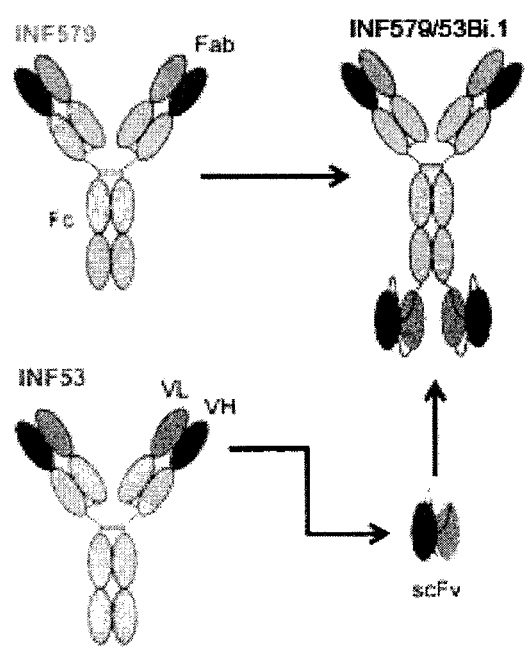

The construction of MAB579/53Bi provides an scFv portion of MAB53 coupled to the constant region of MAB579 as shown in FIG. 5. Construction of such bispecific antibodies is well known in the art (Marvin, J. S., *Acta Pharmacologica Sinica* (2005) 26:649-658). Thus, MAB579/53Bi provides bivalent binding at both ends of the molecule along with an intact Fc region. Table 4 shows that the bispecific antibody retains the affinity of the independent antibodies as measured by FortéBio™ in nM. The bispecific antibody further retains the neutralization capability of the individual antibodies of which it is composed and has an $EC_{50}$ of 3.5 μg/ml against H1N1; 6.0 μg/ml against H5N1, and 2.2 μg/ml against H3N2.

TABLE 4

Affinity by FortéBio ™ (nM)

| | Strain | MAB53 | MAB579 | Bi-Specific |
|---|---|---|---|---|
| H1 | Calif/07/09 | 0.2 | | 0.3 |
| H5 | Vietnam/1203/2004 | 0.5 | | 2.5 |
| H3 | HongKong/8/1968 | | 0.2 | 0.2 |
| H3 | Perth 16/09 | | 0.7 | 1.3 |
| H7 | Netherlands/219/03 | | 0.4 | 0.3 |

EXAMPLE 6

In Vivo Potency of MAB579/53Bi

In vivo efficacy was measured as described generally in Example 4 with the results as shown in FIGS. 6A-6E.

Figures 6A, 6B, 6C, 6D, 6E:
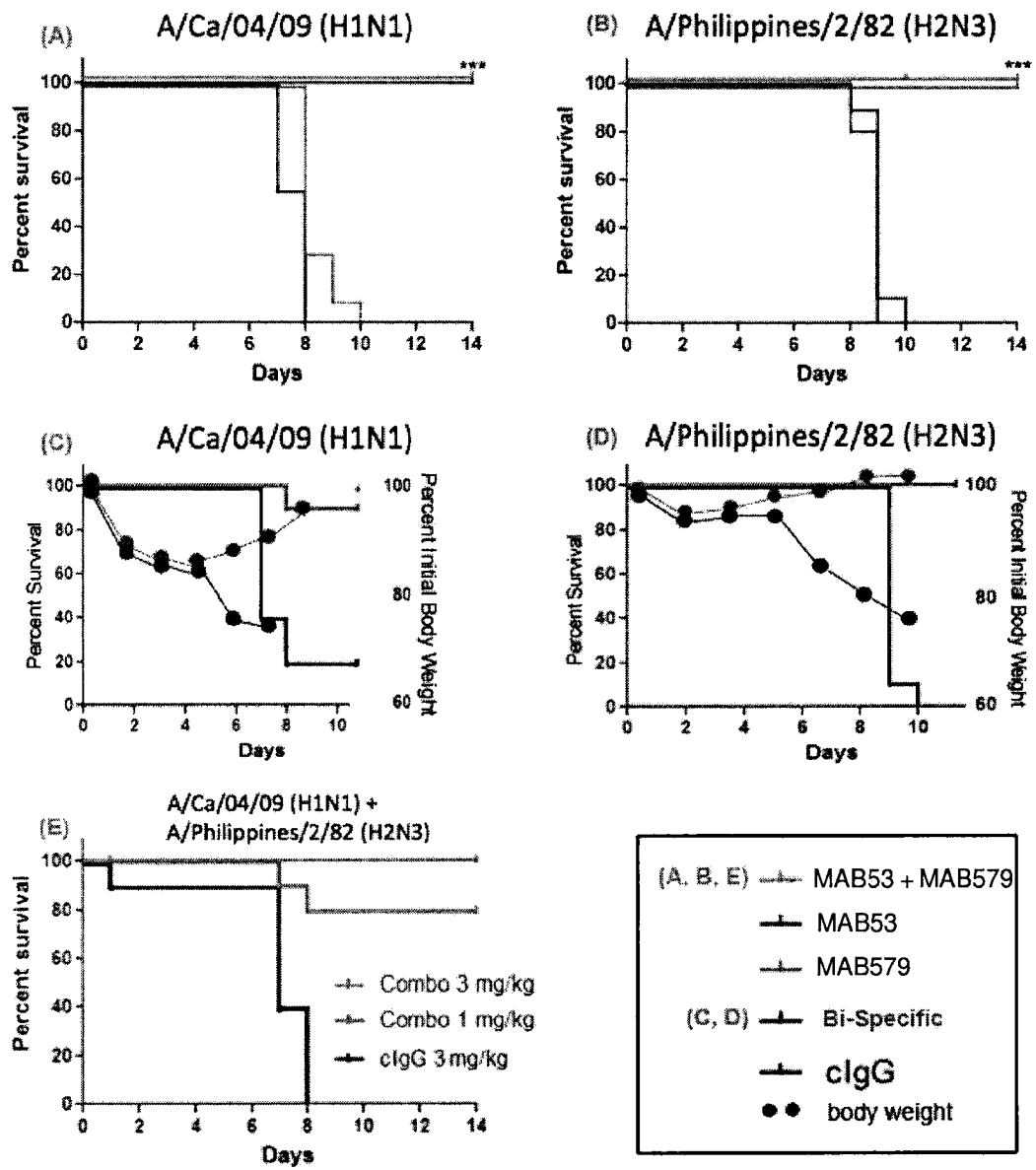

As shown in FIGS. 6A and 6C, mice were infected with A/Ca/04/09 (H1N1) (representing influenza Group 1) on Day 0, and treated by IP injection with 10 mg/ml MAB53 alone, 10 mg/ml MAB579 alone or either a mixture of MAB53 and MAB579 (FIG. 6A) or the bispecific antibody (FIG. 6C) at Day 2, (FIG. 6C also shows weight loss curves). Controls received IgG at 20 mg/kg. The mixture of MAB's was administered at 10 mg/kg each and the bispecific antibody was administered at 10 mg/kg. As shown in FIG. 6A, the mixture of MAB53 and MAB579, as well as MAB53 alone, were protective, while MAB579 and control resulted in no survivors after 10 days. As shown in FIG. 6C, the bispecific antibody was equally effective as the mixture.

Similar results were obtained in the analogous protocol for mice infected with a Group 2 representative Philippines 2/82 (H2N3) as shown in FIGS. 6B and 6D. (FIG. 6D also shows weight loss curves.) As shown in FIG. 6B, the mixture was effective against this virus as was MAB579, but MAB53 alone and control resulted in death after 10 days. In FIG. 6D, it is demonstrated that the bispecific antibody is equally effective as the mixture.

FIG. 6E shows the results of treatment of infection using the analogous protocol where the challenge was with both Group 1 and Group 2 representatives H1N1 and H2N3 which both infected the same mouse. A combination of MAB579 and MAB53 each at 3 mg/kg was completely protective and at 1 mg/kg each protected 80% of the mice. This is significant because co-infection occurs in nature resulting in recombined virus that may cause a pandemic.

The invention claimed is:

1. A monoclonal antibody, or an antigen-binding fragment thereof, which antibody is selected from the group consisting of MAB383, MAB486, MAB579, MAB699, MAB700, MAB708, MAB710, MAB711 and MAB723 and binds to Influenza A HA0 protein and wherein,

- MAB579 is an antibody comprising (i) a heavy chain variable region that comprises CDR1 of the sequence AYTIH (SEQ ID NO:58), and CDR2 of the sequence WINAGNGHTKYSQRFKGR (SEQ ID NO:59), and CDR3 of the sequence GPETYYYDKTNWLNSHPDEYFQH (SEQ ID NO:60); and (ii) a light chain variable region that comprises CDR1 of the sequence RASQTINNYLA (SEQ ID NO:76) and CDR2 of the sequence KASSLES (SEQ ID NO:77) and CDR3 of the sequence QEYNNDSPLT (SEQ ID NO:78);
- MAB699 is an antibody comprising (i) a heavy chain variable region that comprises CDR1 of the sequence SYTLH (SEQ ID NO:61), and CDR2 of the sequence WINAGNGKTKYPPKFRGR (SEQ ID NO:62), and CDR3 of the sequence GPESYYYDRSDWLNSHPDEYFQY (SEQ ID NO:63); and (ii) a light chain variable region that comprises CDR1 of the sequence RASQSISSWLA (SEQ ID NO:79) and CDR2 of the sequence KASQLES (SEQ ID NO:80) and CDR3 of the sequence QLYNVYSPLT (SEQ ID NO:81);
- MAB700 is an antibody comprising (i) a heavy chain variable region that comprises CDR1 of the sequence SFTMH (SEQ ID NO:64), and CDR2 of the sequence WINAGNGKTKYSQKFQGR (SEQ ID NO:65), and CDR3 of the sequence GPETYYYDSSNWLNSHPDEYLQY (SEQ ID NO:66); and (ii) a light chain variable region that comprises CDR1 of the sequence RASQSISSWLA (SEQ ID NO:79) and CDR2 of the sequence KASTLES (SEQ ID NO:82) and CDR3 of the sequence QEYNNNSPLT (SEQ ID NO:83);
- MAB708 is an antibody comprising (i) a heavy chain variable region that comprises CDR1 of the sequence SFTMH (SEQ ID NO:64), and CDR2 of the sequence WINAGNGKTKYSQKFQGR (SEQ ID NO:65), and CDR3 of the sequence GPETYYYDSSNWLNSHPDEYFQH (SEQ ID NO:67); and (ii) a light chain variable region that comprises CDR1 of the sequence RASQSISSWLA (SEQ ID NO:79) and CDR2 of the sequence KASSLES (SEQ ID NO:77) and CDR3 of the sequence QEYNNNSPLT (SEQ ID NO:83);
- MAB710 is an antibody comprising (i) a heavy chain variable region that comprises CDR1 of the sequence SYSVH (SEQ ID NO:68), and CDR2 of the sequence WINAGNGKTKYPQKFKGR (SEQ ID NO:69), and CDR3 of the sequence GPDSYYYDRNDWLNSHPDEYFQH (SEQ ID NO:70); and (ii) a light chain variable region that comprises CDR1 of the sequence RASQSIDSWLA (SEQ ID NO:84) and CDR2 of the sequence KASNLES (SEQ ID NO:85) and CDR3 of the sequence QLYNVHLI (SEQ ID NO:86);
- MAB711 is an antibody comprising (i) a heavy chain variable region that comprises CDR1 of the sequence TYTIH (SEQ ID NO:71), and CDR2 of the sequence WINAANGHTKYSRKLRSR (SEQ ID NO:72), and CDR3 of the sequence GPETYYFDKTNWLNSHPDEYFQH (SEQ ID NO:73) and (ii) a light chain variable region that comprises CDR1 of the sequence RASQSISTWLA (SEQ ID NO:87) and CDR2 of the sequence KASNLES (SEQ ID NO:85) and CDR3 of the sequence QEYNNDSPLI (SEQ ID NO:88);
- MAB723 is an antibody comprising a heavy chain variable region that comprises (i) CDR1 of the sequence SYTLH (SEQ ID NO:61), and CDR2 of the sequence WINAGNGKVKYPRKLQGR (SEQ ID NO:74), and CDR3 of the sequence GPESYFFDTSNHLNSHPDEYFQF (SEQ ID NO:75); and (ii) a light chain variable region that comprises CDR1 of the sequence RASQSISSYLA (SEQ ID NO:89) and CDR2 of the sequence KASNLES (SEQ ID NO:85) and CDR3 of the sequence QEYNNNSPLT (SEQ ID NO:83);
- MAB383 is an antibody comprising a heavy chain that comprises the sequence QVQLVQSGAEVKRPGASVKVSCRASGYTFTSFGFSWVRQAPGQGLEWMGWISAYNGD TKSPQKLQGRVTMTTDTSTNTAYMELRSLISDDTAVYYCARAPPLYYSSWSSDYWGQG TLLTVSS (SEQ ID NO:4) and a light chain that comprises the sequence DIQMTQSPGTLSLSPGERATLSCRASQSVSSNYLAWYQQKHGQAPRPLIYGASRRATDV PDRFSGSGSGTDFTLTISRLEPEDFAVYYCQQYGSSPRTFGQGTKLEIK (SEQ ID NO:5); and
- MAB486 is an antibody comprising a heavy chain that comprises the QVQLVESGGGMVQPGGSRRLSCAASGFSFSTYGMHWVRQAPGKGLEWVAVISYDGEK QYYLDSVKGRFTISRDNSKDTLYLQMNSLTAEDTAVYYCVKESARRLLRYFEWLLSSPF DNWGQGALVTVSS (SEQ ID NO:6) and a light chain that comprises the sequence DIVMTQSPDSLAVSLGERATINCKSSQTVLYTSNKKNYLAWYQQKPGQPPKLLIYWAST RESGVPDRFSGSGSGTDFTLTISSLQAEDVAVYYCQQYYTSPYTFGQ GTKLEIK (SEQ ID NO:7).

2. The antibody or antigen-binding fragment thereof of claim 1 wherein

MAB579 is an antibody comprising a heavy chain comprising the sequence QVQLVQSGAEVKKPGASVKVSCKTSGYTFTAYTIHWVRQAPGQRLEWMGWINAGNGH TKYSQRFKGRVTITRDTSARTTYMELRSLTSEDTALYFCARGPETYYYDKTNWLNSHPD EYFQHWGHGTQVTVSS (SEQ ID NO:8);

MAB699 is an antibody comprising a heavy chain comprising the sequence QLQLVQSGAEVKKPGAS-VKLSCKASGYTFTSYTLHWVRQAPGQTLEW-MGWINAGNGK TKYPPKFRGRVTITRDTSATTVDMHLSSLTSED-TAVYFCARGPESYYYDRSDWLNSHPD EYFQY-WGQGTLVIVSS (SEQ ID NO:10);

MAB700 is an antibody comprising a heavy chain comprising the sequence QVQLVESGADVKKPGASVT-VSCKASGYTFRSFTMHWVRQVPGQRLEWMGW INAGNGKTKYSQKFQGRVIVTRDTSAS-TAYMELSSLTSEDTAVYYCARGPETYYYDSSN WLNSHPDEYLQYWGQGTPVTVSS (SEQ ID NO:12);

MAB708 is an antibody comprising a heavy chain comprising the sequence QVQLVQSGADVKRPGASVT-VSCKASGYTFRSFTMHWVRQVPGQRLEWMGW INAGNGKTKYSQKFQGRVIVTRDTSAN-TAYMELSSLTSEDTAVYYCARGPETYYYDSSN WLNSHPDEYFQHWGQGTPVTVSS (SEQ ID NO:14);

MAB710 is an antibody comprising a heavy chain comprising the sequence QVQLQESGAEVKKPGAS-VQVSCKASGYTFTSYSVHWVRQAPGQRPEW-MGWI NAGNGKTKYPQKFKGRVTITRDTLARTVNI-HLSSLTSEDTAVYFCARGPDSYYYDRND WLN-SHPDEYFQHWGQGTVVIVSS (SEQ ID NO:16);

MAB711 is an antibody comprising a heavy chain comprising the sequence QVQLVESGAEVKKPGAS-VKITCEASGYTFNTYTIHWLRQAPGQRLEWMG-WIN AANGHTKYSRKLRSRVTIKRDTSARTSYMELSS-LGSEDTAVYYCARGPETYYFDKTNW LNSHP-DEYFQHWGQGTLVTVSS (SEQ ID NO:18); and MAB723 is an antibody having a heavy chain comprising the sequence QVQLVQSGAAVNKPGASVKVSCK-ASGYSFTSYTLHWVRQAPGQRPEWIGWI NAGNGKVKYPRKLQGRITITRDVSATTVHMEL-RSLTSEDTGLYYCARGPESYFFDTSNH LNSHP-DEYFQFWGQGTLVTVSS (SEQ ID NO:20).

3. The antibody or antigen-binding fragment thereof of claim 2, wherein

MAB579 is an antibody comprising a light chain having the sequence DIQMTQSPSTLSASVGDRVTIT-CRASQTINNYLAWYQQKPGKAPKLLI-YKASSLESGVPS RFSGSGSGTEFTLTISSLQPDD-FATYYCQEYNNDSPLTFGGGTKVEIK (SEQ ID NO:9);

MAB699 is an antibody comprising a light chain having the sequence DIQMTQSPSTLSASVGDRVTIA-CRASQSISSWLAWYQQKPGKAPKLLI-YKASQLESGVPS RFSGSGSGTEFTLTINSLQPDD-FATYYCQLYNVYSPLTFGGGTRVDIK (SEQ ID NO:11);

MAB700 is an antibody comprising a light chain having the sequence DIVLTQSPSTLSASVGDRVTIT-CRASQSISSWLAWYQQKPGKAPKLLI-YKASTLESGVPSR FSGSGSGTEFTLTISSLQPDD-FATYYCQEYNNNSPLTFGGGTKVEIK (SEQ ID NO:13);

MAB708 is an antibody comprising a light chain having the sequence DIQMTQSPSTLPASVGDRVTIT-CRASQSISSWLAWYQQKPGKAPKLLI-YKASSLESGVPS RFSGSGSGTEFTLTISSLQPDD-FATYYCQEYNNNSPLTFGGGTKVEIK (SEQ ID NO:15);

MAB710 is an antibody comprising a light chain having the sequence DIVMTQSPSTLSAS-VGDRVTISCRASQSIDSWLAWYQQKPGKAP-KLLIYKASNLESGVPS RFSGSGSGTEFTLTISS-LQPDDFATYYCQLYNVHLITFGGGTRVDIK (SEQ ID NO:17);

MAB711 is an antibody comprising a light chain having the sequence DIVMTQSPSTLSASVGDRVTIT-CRASQSISTWLAWYQQKPGKAPKLLIYKASN-LESGVPARFSGSGSGTEFTLTISSLQPDDFATYYC-QEYNNDSPLILGGGTTVEIK (SEQ ID NO:19); and MAB723 is an antibody comprising a light chain having the sequence DIQMTQSPSTLSASVGDRVTIT-CRASQSISSYLAWYQQKPGKAPKLLIYKASN-LESGVPS RFSGSGSGTEFTLTISSLQPDDFATYY-CQEYNNNSPLTFGAGTKVEIK (SEQ ID NO:21).

4. The antibody or antigen-binding fragment thereof of claim 2 which is a bispecific antibody and further comprises:
a) a MAB8 heavy chain comprising the sequence EVQLVESGGGLVKPGGSLRLSCAASGFTFSTYT-MSWVRQAPGQGLEWVSSITRTSSNIY YADS-VEGRFTISRDNAKNSLYLQMHSLRVEDTAVYY-CARISGVVGPVPFDYWGQGTLIT VSS (SEQ ID NO:22) or
b) a MAB53 heavy chain comprising the sequence QVQLVQSGAEVRKPGSSVKVSCKVSGGI-IRKYAINWVRQAPGQGLEWMGGIIAIFNTAN YAQKFQGRVTITADESTSTVYMELSSLRSEDTA-LYYCARGMNYYSDYFDYWGQGSLVT VSP (MAB53) (SEQ ID NO:24).

5. The antibody or antigen-binding fragment thereof of claim 4 which
in a) comprises a MAB8 light chain comprising the sequence DIQMTQSPSSLSASVGDRVTIT-CRASQTISKYLNWYQQKPGRAPKLLIYSASS-LQSGVPSR FTGSGSGTDFTLTITSLQPEDFATYY-CQQSYRPSQITFGPGTKVDIK (SEQ ID NO:23) or
in b) comprises a MAB53 light chain comprising the sequence EIVLTQSPGTLSLSPGERATLSCRASQS-VRSNNLAWYQHKPGQAPRLLIFGASSRATGIPD RFSGSGSGTDFTLTISRLEPEDFAVYYCQQYGSS-PALTFGGGTKVEIK (SEQ ID NO:25).

6. The antibody or antigen-binding fragment thereof of claim 2 which is a bispecific antibody and further contains a MAB53 heavy chain variable region that comprises
CDR1 of the sequence KYAIN (SEQ ID NO:90), and
CDR2 of the sequence GIIAIFNTANYAQKFQG (SEQ ID NO:91), and
CDR3 of the sequence GMNYYSDYFDY (SEQ ID NO:92).

7. The antibody or antigen-binding fragment thereof of claim 6 which further contains a MAB53 light chain variable region that comprises
CDR1 of the sequence RASQSVRSNNLA (SEQ ID NO:93) and
CDR2 of the sequence GASSRAT (SEQ ID NO:94) and
CDR3 of the sequence QQYGSSPALT (SEQ ID NO:95).

8. The antibody or antigen-binding fragment thereof of claim 1 which is a bispecific antibody which comprises a first antigen-binding region and a second antigen-binding region, wherein the first antigen-binding region comprises
a MAB579 heavy chain variable region that contains
CDR1 of the sequence AYTIH (SEQ ID NO:58), and
CDR2 of the sequence WINAGNGHTKYSQRFKGR (SEQ ID NO:59), and
CDR3 of the sequence GPETYYYDKTNWLNSHPDEY-FQH (SEQ ID NO:60), and a MAB579 light chain variable region that contains
CDR1 of the sequence RASQTINNYLA (SEQ ID NO:89), and
CDR2 of the sequence KASSLES (SEQ ID NO:77), and
CDR3 of the sequence QEYNNDSPLT (SEQ ID NO:83), and
wherein the second antigen-binding region comprises a MAB53 heavy chain variable region that contains
CDR1 of the sequence KYAIN (SEQ ID NO:90), and
CDR2 of the sequence GIIAIFNTANYAQKFQG (SEQ ID NO:91), and
CDR3 of the sequence GMNYYSDYFDY (SEQ ID NO:92), and
a MAB53 light chain variable region that contains
CDR1 of the sequence RASQSVRSNNLA (SEQ ID NO:93), and
CDR2 of the sequence GASSRAT (SEQ ID NO:94), and
CDR3 of the sequence QQYGSSPALT (SEQ ID NO:95).

9. A pharmaceutical composition comprising the antibody or antigen-binding fragment thereof of claim 1.

10. A method for the treatment or prophylaxis of influenza infection in a subject which method comprises administering to the subject an effective amount of a pharmaceutical composition comprising a monoclonal antibody, or an antigen-binding fragment thereof, which antibody is selected from the group consisting of MAB383, MAB486, MAB579, MAB699, MAB700, MAB708, MAB710, MAB711, and MAB723 and binds to Influenza A HA0 protein;
and wherein,
MAB579 is an antibody comprising (i) a heavy chain variable region that comprises CDR1 of the sequence AYTIH (SEQ ID NO:58), and CDR2 of the sequence WINAGNGHTKYSQRFKGR (SEQ ID NO:59), and CDR3 of the sequence GPETYYYDKTNWLNSHPDEYFQH (SEQ ID NO:60); and (ii) a light chain variable region that comprises CDR1 of the sequence RASQTINNYLA (SEQ ID NO:76) and CDR2 of the sequence KASSLES (SEQ ID NO:77) and CDR3 of the sequence QEYNNDSPLT (SEQ ID NO:78);
MAB699 is an antibody comprising (i) a heavy chain variable region that comprises CDR1 of the sequence SYTLH (SEQ ID NO:61), and CDR2 of the sequence WINAGNGKTKYPPKFRGR (SEQ ID NO:62), and CDR3 of the sequence GPESYYYDRSDWLNSHPDEYFQY (SEQ ID NO:63); and (ii) a light chain variable region that comprises CDR1 of the sequence RASQSISSWLA (SEQ ID NO:79) and CDR2 of the sequence KASQLES (SEQ ID NO:80) and CDR3 of the sequence QLYNVYSPLT (SEQ ID NO:81);
MAB700 is an antibody comprising (i) a heavy chain variable region that comprises CDR1 of the sequence SFTMH (SEQ ID NO:64), and CDR2 of the sequence WINAGNGKTKYSQKFQGR (SEQ ID NO:65), and CDR3 of the sequence GPETYYYDSSNWLNSHPDEYLQY (SEQ ID NO:66); and (ii) a light chain variable region that comprises CDR1 of the sequence RASQSISSWLA (SEQ ID NO:79) and CDR2 of the sequence KASTLES (SEQ ID NO:82) and CDR3 of the sequence QEYNNNSPLT (SEQ ID NO:83);
MAB708 is an antibody comprising (i) a heavy chain variable region that comprises CDR1 of the sequence SFTMH (SEQ ID NO:64), and CDR2 of the sequence WINAGNGKTKYSQKFQGR (SEQ ID NO:65), and CDR3 of the sequence GPETYYYDSSNWLNSHPDEYFQH (SEQ ID NO:67); and (ii) a light chain variable region that comprises CDR1 of the sequence RASQSISSWLA (SEQ ID NO:79) and CDR2 of the sequence KASSLES (SEQ ID NO:77) and CDR3 of the sequence QEYNNNSPLT (SEQ ID NO:83);
MAB710 is an antibody comprising (i) a heavy chain variable region that comprises CDR1 of the sequence SYSVH (SEQ ID NO:68), and CDR2 of the sequence WINAGNGKTKYPQKFKGR (SEQ ID NO:69), and CDR3 of the sequence GPDSYYYDRNDWLNSHPDEYFQH (SEQ ID NO:70); and (ii) a light chain variable region that comprises CDR1 of the sequence RASQSIDSWLA (SEQ ID NO:84) and CDR2 of the sequence KASNLES (SEQ ID NO:85) and CDR3 of the sequence QLYNVHLI (SEQ ID NO:86);
MAB711 is an antibody comprising (i) a heavy chain variable region that comprises CDR1 of the sequence TYTIH (SEQ ID NO:71), and CDR2 of the sequence WINAANGHTKYSRKLRSR (SEQ ID NO:72), and CDR3 of the sequence GPETYYFDKTNWLNSHPDEYFQH (SEQ ID NO:73) and (ii) a light chain variable region that comprises CDR1 of the sequence RASQSISTWLA (SEQ ID NO:87) and CDR2 of the sequence KASNLES (SEQ ID NO:85) and CDR3 of the sequence QEYNNDSPLI (SEQ ID NO:88);
MAB723 is an antibody comprising a heavy chain variable region that comprises (i) CDR1 of the sequence SYTLH (SEQ ID NO:61), and CDR2 of the sequence WINAGNGKVKYPRKLQGR (SEQ ID NO:74), and CDR3 of the sequence GPESYFFDTSNHLNSHPDEYFQF (SEQ ID NO:75); and (ii) a light chain variable region that comprises CDR1 of the sequence RASQSISSYLA (SEQ ID NO:89) and CDR2 of the sequence KASNLES (SEQ ID NO:85) and CDR3 of the sequence QEYNNNSPLT (SEQ ID NO:83);
MAB383 is an antibody comprising a heavy chain that comprises the sequence QVQLVQSGAEVKRPGASVKVSCRASGYTFTSFGFSWVRQAPGQGLEWMGWISAYNGD TKSPQKLQGRVTMTTDTSTNTAYMELRSLISDDTAVYYCARAPPLYYSSWSSDYWGQG TLLTVSS (SEQ ID NO:4) and a light chain that comprises the sequence DIQMTQSPGTLSLSPGERATLSCRASQSVSSNYLAWYQQKHGQAPRPLIYGASRRATDV PDRFSGSGSGTDFTLTISRLEPEDFAVYYCQQYGSSPRTFGQGTKLEIK (SEQ ID NO:5); and
MAB 486 is an antibody comprising a heavy chain that comprises the QVQLVESGGGMVQPGGSRRLSCAASGFSFSTYGMHWVRQAPGKGLEWVAVISYDGEK QYYLDSVKGRFTISRDNSKDTLYLQMNSLTAEDTAVYYCVKESARRLLRYFEWLLSSPF DNWGQGALVTVSS (SEQ ID NO:6) and a light chain that comprises the sequence DIVMTQSPDSLAVSLGERATINCKSSQTVLYTSNKKNYLAWYQQKPGQPPKLLIYWAST RESGVPDRFSGSGSGTDFTLTISSLQAEDVAVYYCQQYYTSPYTFGQGTKLEIK (SEQ ID NO:7).

11. The method of claim 10 wherein the subject is infected with influenza.

12. The method of claim 10 wherein the subject is protected against influenza infection.

13. The antibody or antigen-binding fragment thereof of claim 1, wherein the antibody or antigen-binding fragment thereof is bi-specific.

14. The antibody or antigen-binding fragment thereof of claim 1, wherein the antibody or antigen-binding fragment thereof is human or humanized.

15. A method for the treatment or prophylaxis of influenza infection in a subject which method comprises administering to the subject an effective amount of a pharmaceutical composition comprising a monoclonal antibody or an antigen-binding fragment thereof, which antibody binds to Influenza A HA0 protein, and which antibody is a bispecific antibody which comprises a first antigen-binding region and a second antigen-binding region, wherein the first antigen-binding region comprises a MAB579 heavy chain variable region that contains CDR1 of the sequence AYTIH (SEQ ID NO:58), CDR2 of the sequence WINAGNGHTKYSQRFKGR (SEQ ID NO:59), and CDR3 of the sequence GPETYYYDKTNWLNSHPDEYFQH (SEQ ID NO:60); and a MAB579 light chain variable region that contains CDR1 of the sequence RASQTINNYLA (SEQ ID NO:89), CDR2 of the sequence KASSLES (SEQ ID NO:77), and CDR3 of the sequence QEYNNDSPLT (SEQ ID NO:83); and wherein the second antigen-binding region comprises a MAB53 heavy chain variable region that contains CDR1 of the sequence KYAIN (SEQ ID NO:90), CDR2 of the sequence GIIAIFNTANYAQKFQG (SEQ ID NO:91), and CDR3 of the sequence GMNYYSDYFDY (SEQ ID NO:92); and a MAB53 light chain variable region that contains CDR1 of the sequence RASQSVRSNNLA (SEQ ID NO:93), CDR2 of the sequence GASSRAT (SEQ ID NO:94), and CDR3 of the sequence QQYGSSPALT (SEQ ID NO:95).

* * * * *

SEQUENCE LISTING

```
<160> NUMBER OF SEQ ID NOS: 95

<210> SEQ ID NO 1
<211> LENGTH: 330
<212> TYPE: PRT
<213> ORGANISM: Homo sapiens
<220> FEATURE:
<221> NAME/KEY: CHAIN
<222> LOCATION: (1)...(330)
<223> OTHER INFORMATION: IgG1 heavy chain  sequence of constant region

<400> SEQUENCE: 1

Ala Ser Thr Lys Gly Pro Ser Val Phe Pro Leu Val Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 2
<211> LENGTH: 107
<212> TYPE: PRT
<213> ORGANISM: Homo sapiens
<220> FEATURE:
<221> NAME/KEY: CHAIN
<222> LOCATION: (1)...(107)
<223> OTHER INFORMATION: light chain sequence of constant kappa region

<400> SEQUENCE: 2

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 3
<211> LENGTH: 106
<212> TYPE: PRT
<213> ORGANISM: Homo sapiens
<220> FEATURE:
<221> NAME/KEY: CHAIN
<222> LOCATION: (1)...(106)
<223> OTHER INFORMATION: light chain sequence of constant lambda region

<400> SEQUENCE: 3

```
Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
            20                  25                  30
Phe Tyr Pro Gly Ala Val Thr Val Ala Trp Lys Ala Asp Ser Ser Pro
        35                  40                  45
Val Lys Ala Gly Val Glu Thr Thr Thr Pro Ser Lys Gln Ser Asn Asn
    50                  55                  60
Lys Tyr Ala Ala Ser Ser Tyr Leu Ser Leu Thr Pro Glu Gln Trp Lys
65                  70                  75                  80
Ser His Arg Ser Tyr Ser Cys Gln Val Thr His Glu Gly Ser Thr Val
                85                  90                  95
```

```
Glu Lys Thr Val Val Pro Ala Glu Cys Ser
            100                 105

<210> SEQ ID NO 4
<211> LENGTH: 122
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(122)
<223> OTHER INFORMATION: MAB383 heavy chain sequence of variable domain

<400> SEQUENCE: 4

Gln Val Gln Leu Val Gln Ser Gly Ala Glu Val Lys Arg Pro Gly Ala
1               5                   10                  15

Ser Val Lys Val Ser Cys Arg Ala Ser Gly Tyr Thr Phe Thr Ser Phe
            20                  25                  30

Gly Phe Ser Trp Val Arg Gln Ala Pro Gly Gln Gly Leu Glu Trp Met
        35                  40                  45

Gly Trp Ile Ser Ala Tyr Asn Gly Asp Thr Lys Ser Pro Gln Lys Leu
    50                  55                  60

Gln Gly Arg Val Thr Met Thr Thr Asp Thr Ser Thr Asn Thr Ala Tyr
65                  70                  75                  80

Met Glu Leu Arg Ser Leu Ile Ser Asp Asp Thr Ala Val Tyr Tyr Cys
                85                  90                  95

Ala Arg Ala Pro Pro Leu Tyr Tyr Ser Ser Trp Ser Ser Asp Tyr Trp
            100                 105                 110

Gly Gln Gly Thr Leu Leu Thr Val Ser Ser
        115                 120

<210> SEQ ID NO 5
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB383 light chain sequence of variable domain

<400> SEQUENCE: 5

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys His Gly Gln Ala Pro Arg Pro Leu
        35                  40                  45

Ile Tyr Gly Ala Ser Arg Arg Ala Thr Asp Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Leu Glu Ile Lys
            100                 105

<210> SEQ ID NO 6
<211> LENGTH: 129
```

```
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(129)
<223> OTHER INFORMATION: MAB486 heavy chain sequence of variable domain

<400> SEQUENCE: 6

Gln Val Gln Leu Val Glu Ser Gly Gly Gly Met Val Gln Pro Gly Gly
1               5                   10                  15

Ser Arg Arg Leu Ser Cys Ala Ala Ser Gly Phe Ser Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Glu Lys Gln Tyr Tyr Leu Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Thr Ala Glu Asp Thr Ala Val Tyr Tyr Cys
                85                  90                  95

Val Lys Glu Ser Ala Arg Arg Leu Leu Arg Tyr Phe Glu Trp Leu Leu
            100                 105                 110

Ser Ser Pro Phe Asp Asn Trp Gly Gln Gly Ala Leu Val Thr Val Ser
        115                 120                 125

Ser

<210> SEQ ID NO 7
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(113)
<223> OTHER INFORMATION: MAB486 light chain sequence of variable domain

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Leu Tyr Thr
            20                  25                  30

Ser Asn Lys Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Ser Pro Tyr Thr Phe Gly Gln Gly Thr Lys Leu Glu Ile
            100                 105                 110

Lys

<210> SEQ ID NO 8
<211> LENGTH: 132
<212> TYPE: PRT
<213> ORGANISM: Artificial Sequence
```

```
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB579 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ala Tyr
            20                  25                  30

Thr Ile His Trp Val Arg Gln Ala Pro Gly Gln Arg Leu Glu Trp Met
        35                  40                  45

Gly Trp Ile Asn Ala Gly Asn Gly His Thr Lys Tyr Ser Gln Arg Phe
50                  55                  60

Lys Gly Arg Val Thr Ile Thr Arg Asp Thr Ser Ala Arg Thr Thr Tyr
65                  70                  75                  80

Met Glu Leu Arg Ser Leu Thr Ser Glu Asp Thr Ala Leu Tyr Phe Cys
                85                  90                  95

Ala Arg Gly Pro Glu Thr Tyr Tyr Tyr Asp Lys Thr Asn Trp Leu Asn
            100                 105                 110

Ser His Pro Asp Glu Tyr Phe Gln His Trp Gly His Gly Thr Gln Val
        115                 120                 125

Thr Val Ser Ser
    130

<210> SEQ ID NO 9
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB579 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Asn Asn Tyr
            20                  25                  30
```

-continued

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Glu Tyr Asn Asn Asp Ser Pro
                 85                  90                  95

Leu Thr Phe Gly Gly Gly Thr Lys Val Glu Ile Lys
            100                 105

<210> SEQ ID NO 10
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB699 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 10

Gln Leu Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ser Tyr
             20                  25                  30

Thr Leu His Trp Val Arg Gln Ala Pro Gly Gln Thr Leu Glu Trp Met
            35                  40                  45

Gly Trp Ile Asn Ala Gly Asn Gly Lys Thr Lys Tyr Pro Pro Lys Phe
 50                  55                  60

Arg Gly Arg Val Thr Ile Thr Arg Asp Thr Ser Ala Thr Thr Val Asp
 65                  70                  75                  80

Met His Leu Ser Ser Leu Thr Ser Glu Asp Thr Ala Val Tyr Phe Cys
                 85                  90                  95

Ala Arg Gly Pro Glu Ser Tyr Tyr Tyr Asp Arg Ser Asp Trp Leu Asn
            100                 105                 110

Ser His Pro Asp Glu Tyr Phe Gln Tyr Trp Gly Gln Gly Thr Leu Val
            115                 120                 125

Ile Val Ser Ser
    130

<210> SEQ ID NO 11
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
```

```
<223> OTHER INFORMATION: MAB699 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(56)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 11

Asp Ile Gln Met Thr Gln Ser Pro Ser Thr Leu Ser Ala Ser Val Gly
1               5                   10                  15

Asp Arg Val Thr Ile Ala Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Gln Leu Glu Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Leu Tyr Asn Val Tyr Ser Pro
                85                  90                  95

Leu Thr Phe Gly Gly Gly Thr Arg Val Asp Ile Lys
            100                 105

<210> SEQ ID NO 12
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB700 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 12

Gln Val Gln Leu Val Glu Ser Gly Ala Asp Val Lys Lys Pro Gly Ala
1               5                   10                  15

Ser Val Thr Val Ser Cys Lys Ala Ser Gly Tyr Thr Phe Arg Ser Phe
            20                  25                  30

Thr Met His Trp Val Arg Gln Val Pro Gly Gln Arg Leu Glu Trp Met
        35                  40                  45

Gly Trp Ile Asn Ala Gly Asn Gly Lys Thr Lys Tyr Ser Gln Lys Phe
50                  55                  60

Gln Gly Arg Val Ile Val Thr Arg Asp Thr Ser Ala Ser Thr Ala Tyr
65                  70                  75                  80

Met Glu Leu Ser Ser Leu Thr Ser Glu Asp Thr Ala Val Tyr Tyr Cys
```

```
                        85                  90                  95
Ala Arg Gly Pro Glu Thr Tyr Tyr Asp Ser Ser Asn Trp Leu Asn
                100                 105                 110

Ser His Pro Asp Glu Tyr Leu Gln Tyr Trp Gly Gln Gly Thr Pro Val
            115                 120                 125

Thr Val Ser Ser
        130

<210> SEQ ID NO 13
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB700 light chain sequence of variable domain
<220> FEATURE:
<221> NAME/KEY: DOMAIN
<222> LOCATION: (25)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 13

Asp Ile Val Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Asn Ser Pro
                85                  90                  95

Leu Thr Phe Gly Gly Gly Thr Lys Val Glu Ile Lys
            100                 105

<210> SEQ ID NO 14
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB708 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
```

```
<222> LOCATION: (99)...(121)
<223> OTHER INFORMATION: CDR3

<400> SEQUENCE: 14

Gln Val Gln Leu Val Gln Ser Gly Ala Asp Val Lys Arg Pro Gly Ala
1               5                   10                  15

Ser Val Thr Val Ser Cys Lys Ala Ser Gly Tyr Thr Phe Arg Ser Phe
            20                  25                  30

Thr Met His Trp Val Arg Gln Val Pro Gly Gln Arg Leu Glu Trp Met
        35                  40                  45

Gly Trp Ile Asn Ala Gly Asn Gly Lys Thr Lys Tyr Ser Gln Lys Phe
    50                  55                  60

Gln Gly Arg Val Ile Val Thr Arg Asp Thr Ser Ala Asn Thr Ala Tyr
65                  70                  75                  80

Met Glu Leu Ser Ser Leu Thr Ser Glu Asp Thr Ala Val Tyr Tyr Cys
                85                  90                  95

Ala Arg Gly Pro Glu Thr Tyr Tyr Tyr Asp Ser Ser Asn Trp Leu Asn
            100                 105                 110

Ser His Pro Asp Glu Tyr Phe Gln His Trp Gly Gln Gly Thr Pro Val
        115                 120                 125

Thr Val Ser Ser
    130

<210> SEQ ID NO 15
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB708 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 15

Asp Ile Gln Met Thr Gln Ser Pro Ser Thr Leu Pro Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu Tyr Asn Asn Asn Ser Pro
                85                  90                  95

Leu Thr Phe Gly Gly Gly Thr Lys Val Glu Ile Lys
            100                 105
```

<210> SEQ ID NO 16
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB710 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 16

```
Gln Val Gln Leu Gln Glu Ser Gly Ala Glu Val Lys Pro Gly Ala
1               5                   10                  15

Ser Val Gln Val Ser Cys Lys Ala Ser Gly Tyr Thr Phe Thr Ser Tyr
            20                  25                  30

Ser Val His Trp Val Arg Gln Ala Pro Gly Gln Arg Pro Glu Trp Met
        35                  40                  45

Gly Trp Ile Asn Ala Gly Asn Gly Lys Thr Lys Tyr Pro Gln Lys Phe
50                  55                  60

Lys Gly Arg Val Thr Ile Thr Arg Asp Thr Leu Ala Arg Thr Val Asn
65                  70                  75                  80

Ile His Leu Ser Ser Leu Thr Ser Glu Asp Thr Ala Val Tyr Phe Cys
                85                  90                  95

Ala Arg Gly Pro Asp Ser Tyr Tyr Asp Arg Asn Asp Trp Leu Asn
            100                 105                 110

Ser His Pro Asp Glu Tyr Phe Gln His Trp Gly Gln Gly Thr Val Val
        115                 120                 125

Ile Val Ser Ser
        130
```

<210> SEQ ID NO 17
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(107)
<223> OTHER INFORMATION: MAB710 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(96)
<223> OTHER INFORMATION: CDR3

<400> SEQUENCE: 17

-continued

Asp Ile Val Met Thr Gln Ser Pro Ser Thr Leu Ser Ala Ser Val Gly
1               5                   10                  15

Asp Arg Val Thr Ile Ser Cys Arg Ala Ser Gln Ser Ile Asp Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Leu Tyr Asn Val His Leu Ile
                85                  90                  95

Thr Phe Gly Gly Gly Thr Arg Val Asp Ile Lys
            100                 105

<210> SEQ ID NO 18
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB711 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 18

Gln Val Gln Leu Val Glu Ser Gly Ala Glu Val Lys Lys Pro Gly Ala
1               5                   10                  15

Ser Val Lys Ile Thr Cys Glu Ala Ser Gly Tyr Thr Phe Asn Thr Tyr
            20                  25                  30

Thr Ile His Trp Leu Arg Gln Ala Pro Gly Gln Arg Leu Glu Trp Met
        35                  40                  45

Gly Trp Ile Asn Ala Ala Asn Gly His Thr Lys Tyr Ser Arg Lys Leu
50                  55                  60

Arg Ser Arg Val Thr Ile Lys Arg Asp Thr Ser Ala Arg Thr Ser Tyr
65                  70                  75                  80

Met Glu Leu Ser Ser Leu Gly Ser Glu Asp Thr Ala Val Tyr Tyr Cys
                85                  90                  95

Ala Arg Gly Pro Glu Thr Tyr Tyr Phe Asp Lys Thr Asn Trp Leu Asn
            100                 105                 110

Ser His Pro Asp Glu Tyr Phe Gln His Trp Gly Gln Gly Thr Leu Val
        115                 120                 125

Thr Val Ser Ser
    130

<210> SEQ ID NO 19
<211> LENGTH: 108
<212> TYPE: PRT
<213> ORGANISM: Artificial Sequence

```
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB711 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 19

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Thr Trp
             20                  25                  30

Leu Ala Trp Tyr Gln Gln Lys Pro Gly Lys Ala Pro Lys Leu Leu Ile
         35                  40                  45

Tyr Lys Ala Ser Asn Leu Glu Ser Gly Val Pro Ala Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Glu Tyr Asn Asn Asp Ser Pro
                 85                  90                  95

Leu Ile Leu Gly Gly Gly Thr Thr Val Glu Ile Lys
            100                 105

<210> SEQ ID NO 20
<211> LENGTH: 132
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(132)
<223> OTHER INFORMATION: MAB723 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (49)...(67)
<223> OTHER INFORMATION: CDR2
<220> FEATURE:
<221> NAME/KEY: DOMAIN
<222> LOCATION: (99)...(121)
<223> OTHER INFORMATION: CDR3

<400> SEQUENCE: 20

Gln Val Gln Leu Val Gln Ser Gly Ala Ala Val Asn Lys Pro Gly Ala
 1               5                  10                  15

Ser Val Lys Val Ser Cys Lys Ala Ser Gly Tyr Ser Phe Thr Ser Tyr
             20                  25                  30

Thr Leu His Trp Val Arg Gln Ala Pro Gly Gln Arg Pro Glu Trp Ile
         35                  40                  45

Gly Trp Ile Asn Ala Gly Asn Gly Lys Val Lys Tyr Pro Arg Lys Leu
 50                  55                  60
```

```
Gln Gly Arg Ile Thr Ile Thr Arg Asp Val Ser Ala Thr Thr Val His
 65                  70                  75                  80

Met Glu Leu Arg Ser Leu Thr Ser Glu Asp Thr Gly Leu Tyr Tyr Cys
                 85                  90                  95

Ala Arg Gly Pro Glu Ser Tyr Phe Phe Asp Ser Asn His Leu Asn
            100                 105                 110

Ser His Pro Asp Glu Tyr Phe Gln Phe Trp Gly Gln Gly Thr Leu Val
        115                 120                 125

Thr Val Ser Ser
        130

<210> SEQ ID NO 21
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB723 light chain sequence of variable domain
<220> FEATURE:
<221> NAME/KEY: DOMAIN
<222> LOCATION: (24)...(34)
<223> OTHER INFORMATION: CDR1
<220> FEATURE:
<221> NAME/KEY: DOMAIN
<222> LOCATION: (50)...(57)
<223> OTHER INFORMATION: CDR2
<220> FEATURE:
<221> NAME/KEY: DOMAIN
<222> LOCATION: (89)...(98)
<223> OTHER INFORMATION: CDR3

<400> SEQUENCE: 21

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Ala Trp Tyr Gln Gln Lys Pro Gly Lys Ala Pro Lys Leu Leu Ile
             35                  40                  45

Tyr Lys Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Glu Tyr Asn Asn Asn Ser Pro
                 85                  90                  95

Leu Thr Phe Gly Ala Gly Thr Lys Val Glu Ile Lys
            100                 105

<210> SEQ ID NO 22
<211> LENGTH: 121
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(121)
<223> OTHER INFORMATION: MAB8 heavy chain sequence of variable domain

<400> SEQUENCE: 22

Glu Val Gln Leu Val Glu Ser Gly Gly Gly Leu Val Lys Pro Gly Gly
  1               5                  10                  15
```

```
Ser Leu Arg Leu Ser Cys Ala Ala Ser Gly Phe Thr Phe Ser Thr Tyr
            20                  25                  30

Thr Met Ser Trp Val Arg Gln Ala Pro Gly Gln Gly Leu Glu Trp Val
            35                  40                  45

Ser Ser Ile Thr Arg Thr Ser Ser Asn Ile Tyr Tyr Ala Asp Ser Val
50                  55                  60

Glu Gly Arg Phe Thr Ile Ser Arg Asp Asn Ala Lys Asn Ser Leu Tyr
65                  70                  75                  80

Leu Gln Met His Ser Leu Arg Val Glu Asp Thr Ala Val Tyr Tyr Cys
                85                  90                  95

Ala Arg Ile Ser Gly Val Val Gly Pro Val Pro Phe Asp Tyr Trp Gly
            100                 105                 110

Gln Gly Thr Leu Ile Thr Val Ser Ser
            115                 120

<210> SEQ ID NO 23
<211> LENGTH: 108
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(108)
<223> OTHER INFORMATION: MAB8 light chain sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Lys Tyr
            20                  25                  30

Leu Asn Trp Tyr Gln Gln Lys Pro Gly Arg Ala Pro Lys Leu Leu Ile
            35                  40                  45

Tyr Ser Ala Ser Ser Leu Gln Ser Gly Val Pro Ser Arg Phe Thr Gly
50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Tyr Arg Pro Ser Gln
                85                  90                  95

Ile Thr Phe Gly Pro Gly Thr Lys Val Asp Ile Lys
            100                 105

<210> SEQ ID NO 24
<211> LENGTH: 120
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(120)
<223> OTHER INFORMATION: MAB53 heavy chain sequence of variable domain
<220> FEATURE:
<221> NAME/KEY: DOMAIN
<222> LOCATION: (31)...(35)
<223> OTHER INFORMATION: CDR1
<220> FEATURE:
<221> NAME/KEY: DOMAIN
<222> LOCATION: (50)...(66)
<223> OTHER INFORMATION: CDR2
<220> FEATURE:
<221> NAME/KEY: DOMAIN
<222> LOCATION: (99)...(110)
```

<223> OTHER INFORMATION: CDR3

<400> SEQUENCE: 24

Gln Val Gln Leu Val Gln Ser Gly Ala Glu Val Arg Lys Pro Gly Ser
1               5                   10                  15

Ser Val Lys Val Ser Cys Lys Val Ser Gly Gly Ile Ile Arg Lys Tyr
            20                  25                  30

Ala Ile Asn Trp Val Arg Gln Ala Pro Gly Gln Gly Leu Glu Trp Met
        35                  40                  45

Gly Gly Ile Ile Ala Ile Phe Asn Thr Ala Asn Tyr Ala Gln Lys Phe
50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Gly Met Asn Tyr Tyr Ser Asp Tyr Phe Asp Tyr Trp Gly Gln
            100                 105                 110

Gly Ser Leu Val Thr Val Ser Pro
        115                 120

<210> SEQ ID NO 25
<211> LENGTH: 109
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(109)
<223> OTHER INFORMATION: MAB53 light chain sequence
<220> FEATURE:
<221> NAME/KEY: DOMAIN
<222> LOCATION: (24)...(35)
<223> OTHER INFORMATION: CDR1
<220> FEATURE:
<221> NAME/KEY: DOMAIN
<222> LOCATION: (51)...(57)
<223> OTHER INFORMATION: CDR2
<220> FEATURE:
<221> NAME/KEY: DOMAIN
<222> LOCATION: (90)...(98)
<223> OTHER INFORMATION: CDR3

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Asn
            20                  25                  30

Asn Leu Ala Trp Tyr Gln His Lys Pro Gly Gln Ala Pro Arg Leu Leu
        35                  40                  45

Ile Phe Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ala Leu Thr Phe Gly Gly Gly Thr Lys Val Glu Ile Lys
            100                 105

<210> SEQ ID NO 26
<211> LENGTH: 1599
<212> TYPE: DNA

```
<213> ORGANISM: Homo sapiens
<220> FEATURE:
<221> NAME/KEY: misc_feature
<222> LOCATION: (1)...(1599)
<223> OTHER INFORMATION: IgG1 heavy chain sequence of constant region

<400> SEQUENCE: 26
gcctccacca agggcccatc agtcttcccc ctggcaccct ctaccaagag cacctctggg      60
ggcacaacgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttggtgag     300
aggccagcac agggagggag ggtgtctgct ggaagccagg ctcagcgctc ctgcctggac     360
gcatcccggc tatgcagtcc cagtccaggg cagcaaggca ggccccgtct gcctcttcac     420
ccggaggcct ctgcccgccc cactcatgct cagggagagg gtcttctggc tttttcccca     480
ggctctgggc aggcacaggc taggtgcccc taacccaggc cctgcacaca aaggggcagg     540
tgctgggctc agacctgcca agagccatat ccgggaggac cctgccctg acctaagccc      600 accccaaagg ccaaactctc cactccctca gctcggacac tttctctcct cccagattcc     660
agtaactccc aatcttctct ctgcagagcc caaatcttgt gacaaaactc acacatgccc     720
accgtgccca ggtaagccag cccaggcctc gccctccagc tcaaggcggg acaggtgccc     780
tagagtagcc tgcatccagg acaggcccc agccgggtgc tgacacgtcc acctccatct      840
cttcctcagc acctgaactc ctgggggac cgtcagtctt cctcttcccc ccaaaaccca      900
aggacaccct catgatctcc cggacccctg aggtcacatg cgtggtggtg gacgtgagcc     960
acgaagaccc tgaggtcaag ttcaactggt acgtggacgg cgtggaggtg cataatgcca    1020
agacaaagcc gcgggaggag cagtacaaca gcacgtaccg tgtggtcagc gtcctcaccg    1080
tcctgcacca ggactggctg aatggcaagg agtacaagtg caaggtctcc aacaaagccc    1140
tcccagcccc catcgagaaa accatctcca agccaaaagg tgggacccgt ggggtgcgag    1200
ggccacatgg acagaggccg gctcggccca ccctctgccc tgagagtgac cgctgtacca    1260
acctctgtcc ctacagggca gccccgagaa ccacaggtgt acaccctgcc cccatcccgg    1320
gaggagatga ccaagaacca ggtcagcctg acctgcctgg tcaaaggctt ctatcccagc    1380
gacatcgccg tggagtggga gagcaatggg cagccggaga caactacaa gaccacgcct     1440 cccgtgctgg actccgacgg ctccttcttc ctctatagca agctcaccgt ggacaagagc    1500
aggtggcagc aggggaacgt cttctcatgc tccgtgatgc atgaggctct gcacaaccac    1560
tacacgcaga gagcctctc cctgtccccg ggtaaatga                            1599

<210> SEQ ID NO 27
<211> LENGTH: 324
<212> TYPE: DNA
<213> ORGANISM: Homo sapiens
<220> FEATURE:
<221> NAME/KEY: misc_feature
<222> LOCATION: (1)...(324)
<223> OTHER INFORMATION: light chain sequence of constant kappa region

<400> SEQUENCE: 27
cgaactgtgg ctgcaccatc tgtcttcatc ttcccgccat ctgatgagca gttgaaatct      60
ggaactgcta gcgttgtgtg cctgctgaat aacttctatc ccagagaggc caaagtacag     120
tggaaggtgg ataacgccct ccaatcgggt aactcccagg agagtgtcac agagcaggac     180
```

```
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                          324
```

<210> SEQ ID NO 28
<211> LENGTH: 318
<212> TYPE: DNA
<213> ORGANISM: Homo sapiens
<220> FEATURE:
<221> NAME/KEY: misc_feature
<222> LOCATION: (1)...(318)
<223> OTHER INFORMATION: light chain sequence of constant lambda region

<400> SEQUENCE: 28

```
ggtcagccca aggctgcccc ctctgtcact ctgttcccgc cctctagcga ggagcttcaa     60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tatctgagcc tgacgcctga gcagtggaag    240
tcccacagaa gctacagctg ccaggtcacg catgaaggga gcaccgtgga agacagtg     300 gtccctgcag aatgctct                                                  318
```

<210> SEQ ID NO 29
<211> LENGTH: 366
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(366)
<223> OTHER INFORMATION: MAB383 heavy chain sequence of variable domain

<400> SEQUENCE: 29

```
caggtgcagc tggtgcagtc tggagctgag gtgaagaggc ctggggcctc agtgaaggtc     60
tcctgcaggg cttctggtta cacctttact agcttcggtt tcagctgggt gcgacaggcc    120
ccaggacaag gcttgagtg gatggggtgg atcagcgctt acaatggtga cacaaagtct    180
ccacagaagc tccagggcag agtcaccatg actacagaca catccacgaa cacagcctac    240
atggagctga ggagcctcat atctgacgac acggccgtgt attattgtgc gagagccccc    300
cccctgtatt acagtagctg gtcctcagac tactggggcc agggaaccct gctcaccgtc    360
tcctca                                                              366
```

<210> SEQ ID NO 30
<211> LENGTH: 325
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(323)
<223> OTHER INFORMATION: MAB383 light chain sequence of variable domain

<400> SEQUENCE: 30

```
gatatccaga tgacgcagtc tccaggcacc ctgtctttgt ctccagggga aagagccacc     60
ctctcctgca gggccagtca gagtgtcagt agcaactact tagcctggta ccagcagaaa    120
catggccagg ctcccaggcc cctcatctac ggtgcatcca aagggccac tgacgtccca    180
```

```
gacaggttca gtggcagtgg gtctgggaca gacttcactc tcaccatcag cagactggaa    240
cctgaagatt tgcagtgta ttattgtcag cagtatggta gttcacctcg aacttttggc    300
caggggacca aactggaaat caaac                                         325

<210> SEQ ID NO 31
<211> LENGTH: 387
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(387)
<223> OTHER INFORMATION: MAB486 heavy chain sequence of variable domain

<400> SEQUENCE: 31
caggtgcagc tggtggagtc tgggggaggc atggtccagc cggggggtc ccggagactc     60 tcctgtgcag cctctggatt cagcttcagt acctatggca tgcactgggt ccgccaggct   120
ccaggcaagg ggctggagtg gtggcagtt atttcatatg atggagaaaa gcaatattat   180
ctagactccg tgaagggacg attcaccatc tccagacaca attccaagga caccctctat   240
ctgcaaatga acagtctgac agctgaggac acggctgtgt attactgtgt gaaggaatca   300
gcgcgtcgat tattacgata ttttgagtgg ttattaagtt cgccttttga caactggggc   360
cagggagccc tagtcaccgt ctcctca                                      387

<210> SEQ ID NO 32
<211> LENGTH: 339
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(339)
<223> OTHER INFORMATION: MAB486 light chain sequence of variable domain

<400> SEQUENCE: 32
gatatcgtga tgacccagtc tccagactcc ctggctgtgt ctttgggcga gagggccacc    60
atcaactgca gtccagccaa gactgtttta tacacctcca acaagaaaaa ttacttagcc   120
tggtaccaac agaagccagg gcagcctcct aaactgctca tttactgggc atctacccgg   180
gaatccgggg tccctgaccg attcagtggc agcgggtctg ggacagattt cactctcacc   240
atcagcagcc tgcaggctga ggatgtggca gtttattact gtcagcaata ttatacgtct   300
ccctacacat ttggccaggg gaccaagctg gagatcaaa                         339

<210> SEQ ID NO 33
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB579 heavy chain sequence of variable domain

<400> SEQUENCE: 33
caggtgcagc tggtgcagtc tggggctgag gtgaagaagc ctggggcctc agtgaaggtt    60
tcctgcaaga cttctggata caccttcaca gcctatacta tacactgggt gcgccaggcc   120
cccggacaaa ggcttgagtg gatgggatgg atcaacgctg gcaatggtca cacgaaatat   180
```

```
tcacagaggt tcaagggcag agtcaccatt accagggaca catccgcgag acaacctac    240 atggagctgc gcagtctgac atctgaggac acggctctat atttctgtgc gagagggccc    300
gagacatatt attatgataa aaccaattgg ctgaactccc atccagatga atacttccag    360
cactggggcc acggcaccca ggtcaccgtc tcctca                               396
```

<210> SEQ ID NO 34
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB579 light chain sequence of variable domain

<400> SEQUENCE: 34

```
gatatccaga tgacccagtc tccttccacc ctgtctgcat ctgtaggaga cagagtcacc    60
atcacttgcc gggccagtca gactattaat aactacttgg cctggtatca gcagaaacca    120
gggaaagccc ctaaactcct gatctataag gcgtctagtt tagaaagtgg ggtcccatca    180
agattcagtg gcagtgggtc tgggacagaa ttcactctca ccatcagcag cctgcagcct    240
gatgattttg caacttatta ctgccaagaa tataataatg attctcccct aactttcggc    300
ggagggacca agtggagat caaa                                              324
```

<210> SEQ ID NO 35
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB699 heavy chain sequence of variable domain

<400> SEQUENCE: 35

```
caggtgcagc tggtgcagtc cggggctgag gtgaagaagc ctggggcctc agtgaagctt    60
tcctgcaagg cttctgggta caccttcact tcctatactc tacattgggt gcgccaggcc    120
cccggacaga cacttgagtg gatgggatgg atcaacgctg gcaacggtaa aacaaaatat    180
ccaccgaagt tcaggggcag agtcaccatt accaggaca cgtccgcgac cacagtcgac    240
atgcatctaa gcagcctgac atctgaagac acggctgtgt atttctgtgc gagagggccc    300
gaaagttatt actatgatag aagtgattgg ctgaactccc atccagatga atacttccag    360
tactggggcc agggcaccct ggtcatcgtc tcctca                                396
```

<210> SEQ ID NO 36
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB699 light chain sequence of variable domain

<400> SEQUENCE: 36

```
gatatcgtgc tgacgcagtc tccttccacc ctgtctgcat ctgtagggga cagagtcacc    60
```

```
atcgcttgcc gggccagtca gagtattagc agctggctgg cctggtatca gcagaaacca      120
gggaaagccc ctaaactcct gatctacaag gcgtctcagt tagaaagtgg ggtcccatca      180
agattcagcg gcagcggatc tgggacagag ttcactctca ccatcaacag cctgcagcct      240
gatgattttg caacttatta ctgccaactt tataatgttt attctccgct cactttcggc      300 gggggggacca gggtggacat caaa                                            324
```

<210> SEQ ID NO 37
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB700 heavy chain sequence of variable domain

<400> SEQUENCE: 37

```
caggtgcagc tggtggagtc tggggctgac gtgaagaagc tggggcctc agtgacggtt       60 tcctgcaagg cctcaggata caccttcagg agttttacta tgcattgggt gcgccaggtc     120
cccggacaaa ggcttgagtg gatgggatgg atcaacgctg gcaatggtaa aacaaagtat     180
tctcagaagt tccagggcag agtcatcgtt accagggaca catccgcgag cacagcctac     240
atggagctga gcagcctaac atctgaagac acggctgttt attactgtgc gagagggccc     300
gaaacatatt actatgatag tagtaattgg ctgaattccc atccagatga atatctccag     360
tactggggcc agggcacccc ggtcaccgtc tcctca                                396
```

<210> SEQ ID NO 38
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB700 light chain sequence of variable domain

<400> SEQUENCE: 38

```
gatatccaga tgacccagtc tccttccacc ctgtctgcgt ctgtaggaga cagagtcacc       60
atcacttgcc gggccagtca gagtattagt agctggttgg cctggtatca gcagaaacca     120
gggaaagccc ctaaactcct gatctataag gcgtctactt tagaaagtgg ggtcccatcc     180
aggttcagcg gcagtggatc tgggacagaa ttcactctca ccatcagcag cctgcagcct     240
gatgattttg caacttatta ctgccaagag tataataata attctccgct cactttcggc     300
ggagggacca aggtggagat caaa                                             324
```

<210> SEQ ID NO 39
<211> LENGTH: 366
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(366)
<223> OTHER INFORMATION: MAB708 heavy chain sequence of variable domain

<400> SEQUENCE: 39

```
caggtgcagc tggtgcagtc tggggctgac gtgaagaggc tggggcctc agtgacggtt       60
```

```
tcctgcaagg cttcaggata caccttcagg agctttacta tgcattgggt gcgccaggtc    120
cccggacaaa ggctggagtg gatgggatgg atcaacgctg gcaatggtaa aacaaaatat    180
tcccagaagt ttcagggcag agtcatcgtt accagggaca catccgcgaa cacggcctac    240
atggagctga gcagcctgac atctgaagac acggctgttt attactgtgc gagagggccc    300
gaaacatatt attatgatag tagtaattgg ctgaactccc atccagatga atatttccag    360
cactgg                                                               366

<210> SEQ ID NO 40
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB708 light chain sequence of variable domain

<400> SEQUENCE: 40
gatatccaga tgacccagtc tccttccacc ctgcctgcgt ctgtaggaga cagagtcacc     60
atcacttgcc gggccagtca gagtattagt agctggttgg cctggtatca gcagaaacca    120
gggaaagccc ctaaacttct gatctataag gcgtctagtt tagaaagtgg ggtcccatcc    180
aggttcagcg gcagtggatc tgggacagaa ttcactctca ccatcagcag cctgcagcct    240
gatgattttg caacttatta ctgccaggag tataataata ttctccgctc cactttcggc    300
ggagggacca aggtggagat caaa                                           324

<210> SEQ ID NO 41
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB710 heavy chain sequence of variable domain

<400> SEQUENCE: 41
caagtgcagc tgcaggagtc gggggctgag gtgaagaagc ctggggcctc agtgcaggtt     60
tcctgcaagg cttctgggta caccttcacg tcctatagcg tacattgggt gcgccaggcc    120
cccggacaaa ggcctgagtg gatgggatgg atcaacgctg gcaacggaaa gacaaaatat    180
ccacagaagt tcaagggcag agtcaccata accagagaca cattagcgcg cactgtcaac    240
atacatctaa gcagcctgac atccgaagac acggctgtgt atttctgtgc gagagggccc    300
gatagttatt actatgatag aaatgattgg ctgaactccc atccagatga atacttccag    360
cactggggcc agggcaccgt ggtcatcgtc tcctca                              396

<210> SEQ ID NO 42
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: MAB710 light chain sequence of variable domain
```

<400> SEQUENCE: 42

```
gatatcgtga tgacccagtc tccttccacc ctgtctgcat ctgtgggaga cagagtcacc    60
atctcttgcc gggccagtca gagtattgac agttggttgg cctggtatca gcagaaacca   120
gggaaagccc ctaaactcct gatctataag gcgtctaatt tagaaagtgg ggtcccatca   180
agattcagcg gcagcggatc tgggacagaa ttcactctca ccatcagcag cctgcagcct   240
gatgattttg cgacttatta ctgccaactc tataatgttc atttgatcac tttcggcgga   300
gggaccaggg tggacatcaa a                                             321
```

<210> SEQ ID NO 43
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB711 heavy chain sequence of variable domain

<400> SEQUENCE: 43

```
caggtgcagc tggtggagtc tggggctgag gtgaagaagc ctggggcctc agtgaagatc    60
acctgcgagg cttctggata cactttcaat acctatacta cattggct gcgccaggcc    120
cccggacaaa gacttgagtg gatggggtgg atcaacgctg ccaatggtca tacaaaatat   180
tcacggaagc tcaggtccag agtcaccatt aagagggaca tccgcgagga caagttac    240
atggagctga gcagcctggg atctgaagac acggctgtct attactgtgc gagagggccc   300
gaaacatatt actttgataa gacgaattgg ctgaactccc atccagatga atacttccag   360
cactggggcc agggcaccct ggtcaccgtc tcctca                             396
```

<210> SEQ ID NO 44
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB711 sequence of variable domain

<400> SEQUENCE: 44

```
gatatcgtga tgacgcagtc tccttccacc ctgtctgcat ctgtaggaga cagagtcacc    60
atcacttgcc gggccagtca gagtatttct acctggttgg cctggtatca gcagaaacca   120
gggaaagccc ctaagctcct gatctataag gcgtccaatt tagaaagtgg ggtcccagca   180
agattcagcg gcagtggatc tgggacagag ttcactctca ccatcagcag cctgcagcct   240
gatgattttg caacttatta ctgccaagaa tataataatg attctccgct gattttaggc   300
ggagggacca cggtggagat caaa                                          324
```

<210> SEQ ID NO 45
<211> LENGTH: 396
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(396)
<223> OTHER INFORMATION: MAB723 heavy chain sequence of variable domain

<400> SEQUENCE: 45

```
caggtgcagc tggtgcagtc tggggctgcg gtgaacaagc ctggggcctc agtgaaggtt      60
tcctgcaagg cttctggata cagcttcact agttacactt tgcattgggt gcgccaggcc     120
cccggacaaa ggcctgagtg gatagggtgg atcaacgctg gaatggtaa agtaaaatat     180 ccacggaagt tgcagggcag aatcaccata accaggacg tatccgctac gacagttcac     240
atggaactga ggagcctgac atctgaggac acgggtctat attactgtgc gagagggccc     300
gaaagttact tctttgatac ttctaatcat ctgaactccc atccagatga atacttccag     360
ttctggggcc agggcaccct ggtcaccgtc tcctca                              396
```

<210> SEQ ID NO 46
<211> LENGTH: 324
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(324)
<223> OTHER INFORMATION: MAB723 light chain sequence of variable domain

<400> SEQUENCE: 46

```
gatatcgtgc tgacgcagtc tccttccacc ctgtctgcat ctgtaggaga cagagtcacc      60
atcacttgcc gggccagtca gagtattagt agttacttgg cctggtatca acagaaacca     120
gggaaagccc ctaaactcct gatctataag gcgtctaatt tagaaagtgg ggtcccatca     180
agattcagcg gcagtggatc tgggacagaa ttcactctca ccatcagcag cctgcagcct     240
gatgattttg caacttatta ttgccaagaa tataataata actctccgct cactttcggc     300
gcagggacca aggtggagat caaa                                            324
```

<210> SEQ ID NO 47
<211> LENGTH: 363
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(363)
<223> OTHER INFORMATION: MAB8 heavy chain variable domain sequence

<400> SEQUENCE: 47

```
gaggtgcagc tggtggagtc tgggggaggc ctggtcaagc ctgggggtc cctgagactc      60 tcctgtgcag cctctggttt cactttcagt acctatacta tgagttgggt ccgccaggct     120
ccagggcagg gctagagtg ggtctcgtcc attactagga ctagtagtaa tatatactac     180
gcagactcag tggagggccg attcaccatc tccagagaca acgccaagaa ctcactgtat     240
ctgcagatgc atagcctgag agtcgaagac acggctgtgt attactgtgc gagaatcagc     300
ggggtagtgg gacctgtccc ctttgactac tggggccagg aaccctgat caccgtctcc     360 tct                                                                   363
```

<210> SEQ ID NO 48
<211> LENGTH: 324
<212> TYPE: DNA
<213> ORGANISM: Artificial Sequence
<220> FEATURE:
<223> OTHER INFORMATION: synthetic construct
<220> FEATURE:

```
<221> NAME/KEY: misc_feature
<222> LOCATION: (1)...(324)
<223> OTHER INFORMATION: MAB8 light chain variable domain sequence

<400> SEQUENCE: 48
gacatccaga tgacccagtc tccatcttcc ctgtctgcat ctgtaggaga cagagtcacc    60
atcacttgcc gggcaagtca gaccattagc aagtatttaa attggtatca gcagaagcca   120
gggagagccc ctaaactcct gatctactct gcgtccagtt tgcaaagtgg ggtcccatca   180
aggttcactg gcagtggatc tgggacagat ttcactctca ccatcaccag tctgcaacct   240
gaagattttg caacttacta ctgtcaacag agttacagac cctcccagat cactttcggc   300
cctgggacca aagtggatat caaa                                          324

<210> SEQ ID NO 49
<211> LENGTH: 360
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(360)
<223> OTHER INFORMATION: MAB53 heavy chain variable domain sequence

<400> SEQUENCE: 49
caggtgcagc tggtgcagtc tggggctgag gtgaggaagc cggggtcctc ggtgaaggtc    60
tcctgcaagg tttctggagg catcattagg aaatatgcta tcaactgggt gcgacaggcc   120
cccggacaag gcttgagtg gatgggaggg atcatcgcta tctttaatac agcaaactat   180
gcacagaaat tccagggcag agtcacgatt accgcggacg agtccacgag cacagtctac   240
atggagctga gcagcctgag atctgaagac acggcccttt attactgtgc gagaggaatg   300
aattactaca gtgactactt tgactactgg ggccagggaa gccttgtcac cgtctcccca   360

<210> SEQ ID NO 50
<211> LENGTH: 327
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(327)
<223> OTHER INFORMATION: MAB53 light chain variable domain sequence

<400> SEQUENCE: 50
gaaattgtgt tgacacagtc tccaggcacc ctgtctttgt ctccagggga aagagccacc    60
ctctcctgca gggccagtca gagtgttaga agcaacaact tagcctggta ccagcacaaa   120
cctggccagg ctcccaggct cctcatcttt ggtgcatcca gcagggccac tggcatccca   180
gacaggttca gtggcagtgg gtctgggaca gacttcactc tcaccatcag cagactggag   240
cctgaagatt ttgcagtata ttactgtcag cagtatggta gctcacctgc gctcactttc   300
ggcggaggga ccaaggtgga gatcaaa                                       327

<210> SEQ ID NO 51
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MUTAGEN
```

```
<222> LOCATION: (1)...(8)
<223> OTHER INFORMATION: consensus sequence of influenza A and B virus

<400> SEQUENCE: 51

Asn Val Pro Glu Lys Gln Thr Ar

-continued

```
<212> TYPE: PRT
<213> ORGANISM: Artificial Sequence
<220> FEATURE:
<223> OTHER INFORMATION: synthetic construct
<220> FEATURE:
<221> NAME/KEY: MUTAGEN
<222> LOCATION: (1)...(11)
<223> OTHER INFORMATION: consensus sequence of influenza A and B virus

<400> SEQUENCE: 56

Gly Phe Phe Gly Ala Ile Ala Gly Phe Leu Glu
1               5                   10

<210> SEQ ID NO 57
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MUTAGEN
<222> LOCATION: (1)...(12)
<223> OTHER INFORMATION: consensus sequence
<220> FEATURE:
<221> NAME/KEY: VARIANT
<222> LOCATION: 3
<223> OTHER INFORMATION: Xaa = Ile, Leu, Phe

<400> SEQUENCE: 57

Arg Gly Xaa Phe Gly Ala Ile Ala Gly Phe Leu Glu
1               5                   10

<210> SEQ ID NO 58
<211> LENGTH: 5
<212> TYPE: PRT
<213> ORGANISM: Artificial Sequence
<220> FEATURE:
<223> OTHER INFORMATION: synthetic construct

<400> SEQUENCE: 58

Ala Tyr Thr Ile His
1               5

<210> SEQ ID NO 59
<211> LENGTH: 18
<212> TYPE: PRT
<213> ORGANISM: Artificial Sequence
<220> FEATURE:
<223> OTHER INFORMATION: synthetic construct

<400> SEQUENCE: 59

Trp Ile Asn Ala Gly Asn Gly His Thr Lys Tyr Ser Gln Arg Phe Lys
1               5                   10                  15

Gly Arg

<210> SEQ ID NO 60
<211> LENGTH: 23
<212> TYPE: PRT
<213> ORGANISM: Artificial Sequence
<220> FEATURE:
<223> OTHER INFORMATION: synthetic construct

<400> SEQUENCE: 60

Gly Pro Glu Thr Tyr Tyr Tyr Asp Lys Thr Asn Trp Leu Asn Ser His
1               5                   10                  15

Pro Asp Glu Tyr Phe Gln His
            20

```
<210> SEQ ID NO 61
<211> LENGTH: 5
<212> TYPE: PRT
<213> ORGANISM: Artificial Sequence
<220> FEATURE:
<223> OTHER INFORMATION: synthetic construct

<400> SEQUENCE: 61

Ser Tyr Thr Leu His
1               5

<210> SEQ ID NO 62
<211> LENGTH: 18
<212> TYPE: PRT
<213> ORGANISM: Artificial Sequence
<220> FEATURE:
<223> OTHER INFORMATION: synthetic construct

<400> SEQUENCE: 62

Trp Ile Asn Ala Gly Asn Gly Lys Thr Lys Tyr Pro Pro Lys Phe Arg
1               5                   10                  15

Gly Arg

<210> SEQ ID NO 63
<211> LENGTH: 23
<212> TYPE: PRT
<213> ORGANISM: Artificial Sequence
<220> FEATURE:
<223> OTHER INFORMATION: synthetic construct

<400> SEQUENCE: 63

Gly Pro Glu Ser Tyr Tyr Tyr Asp Arg Ser Asp Trp Leu Asn Ser His
1               5                   10                  15

Pro Asp Glu Tyr Phe Gln Tyr
            20

<210> SEQ ID NO 64
<211> LENGTH: 5
<212> TYPE: PRT
<213> ORGANISM: Artificial Sequence
<220> FEATURE:
<223> OTHER INFORMATION: synthetic construct

<400> SEQUENCE: 64

Ser Phe Thr Met His
1               5

<210> SEQ ID NO 65
<211> LENGTH: 18
<212> TYPE: PRT
<213> ORGANISM: Artificial Sequence
<220> FEATURE:
<223> OTHER INFORMATION: synthetic construct

<400> SEQUENCE: 65

Trp Ile Asn Ala Gly Asn Gly Lys Thr Lys Tyr Ser Gln Lys Phe Gln
1               5                   10                  15

Gly Arg

<210> SEQ ID NO 66
<211> LENGTH: 23
<212> TYPE: PRT
<213> ORGANISM: Artificial Sequence
<220> FEATURE:
<223> OTHER INFORMATION: synthetic construct
```

<400> SEQUENCE: 66

Gly Pro Glu Thr Tyr Tyr Tyr Asp Ser Ser Asn Trp Leu Asn Ser His
1               5                   10                  15

Pro Asp Glu Tyr Leu Gln Tyr
            20

<210> SEQ ID NO 67
<211> LENGTH: 23
<212> TYPE: PRT
<213> ORGANISM: Artificial Sequence
<220> FEATURE:
<223> OTHER INFORMATION: synthetic construct

<400> SEQUENCE: 67

Gly Pro Glu Thr Tyr Tyr Tyr Asp Ser Ser Asn Trp Leu Asn Ser His
1               5                   10                  15

Pro Asp Glu Tyr Phe Gln His
            20

<210> SEQ ID NO 68
<211> LENGTH: 5
<212> TYPE: PRT
<213> ORGANISM: Artificial Sequence
<220> FEATURE:
<223> OTHER INFORMATION: synthetic construct

<400> SEQUENCE: 68

Ser Tyr Ser Val His
1               5

<210> SEQ ID NO 69
<211> LENGTH: 18
<212> TYPE: PRT
<213> ORGANISM: Artificial Sequence
<220> FEATURE:
<223> OTHER INFORMATION: synthetic construct

<400> SEQUENCE: 69

Trp Ile Asn Ala Gly Asn Gly Lys Thr Lys Tyr Pro Gln Lys Phe Lys
1               5                   10                  15

Gly Arg

<210> SEQ ID NO 70
<211> LENGTH: 23
<212> TYPE: PRT
<213> ORGANISM: Artificial Sequence
<220> FEATURE:
<223> OTHER INFORMATION: synthetic construct

<400> SEQUENCE: 70

Gly Pro Asp Ser Tyr Tyr Tyr Asp Arg Asn Asp Trp Leu Asn Ser His
1               5                   10                  15

Pro Asp Glu Tyr Phe Gln His
            20

<210> SEQ ID NO 71
<211> LENGTH: 5
<212> TYPE: PRT
<213> ORGANISM: Artificial Sequence
<220> FEATURE:
<223> OTHER INFORMATION: synthetic construct

<400> SEQUENCE: 71

```
Thr Tyr Thr Ile His
1               5

<210> SEQ ID NO 72
<211> LENGTH: 18
<212> TYPE: PRT
<213> ORGANISM: Artificial Sequence
<220> FEATURE:
<223> OTHER INFORMATION: synthetic construct

<400> SEQUENCE: 72

Trp Ile Asn Ala Ala Asn Gly His Thr Lys Tyr Ser Arg Lys Leu Arg
1               5                   10                  15

Ser Arg

<210> SEQ ID NO 73
<211> LENGTH: 23
<212> TYPE: PRT
<213> ORGANISM: Artificial Sequence
<220> FEATURE:
<223> OTHER INFORMATION: synthetic construct

<400> SEQUENCE: 73

Gly Pro Glu Thr Tyr Tyr Phe Asp Lys Thr Asn Trp Leu Asn Ser His
1               5                   10                  15

Pro Asp Glu Tyr Phe Gln His
            20

<210> SEQ ID NO 74
<211> LENGTH: 18
<212> TYPE: PRT
<213> ORGANISM: Artificial Sequence
<220> FEATURE:
<223> OTHER INFORMATION: synthetic construct

<400> SEQUENCE: 74

Trp Ile Asn Ala Gly Asn Gly Lys Val Lys Tyr Pro Arg Lys Leu Gln
1               5                   10                  15

Gly Arg

<210> SEQ ID NO 75
<211> LENGTH: 23
<212> TYPE: PRT
<213> ORGANISM: Artificial Sequence
<220> FEATURE:
<223> OTHER INFORMATION: synthetic construct

<400> SEQUENCE: 75

Gly Pro Glu Ser Tyr Phe Phe Asp Thr Ser Asn His Leu Asn Ser His
1               5                   10                  15

Pro Asp Glu Tyr Phe Gln Phe
            20

<210> SEQ ID NO 76
<211> LENGTH: 11
<212> TYPE: PRT
<213> ORGANISM: Artificial Sequence
<220> FEATURE:
<223> OTHER INFORMATION: synthetic construct

<400> SEQUENCE: 76

Arg Ala Ser Gln Thr Ile Asn Asn Tyr Leu Ala
1               5                   10
```

```
<210> SEQ ID NO 77
<211> LENGTH: 7
<212> TYPE: PRT
<213> ORGANISM: Artificial Sequence
<220> FEATURE:
<223> OTHER INFORMATION: synthetic construct

<400> SEQUENCE: 77

Lys Ala Ser Ser Leu Glu Ser
1               5

<210> SEQ ID NO 78
<211> LENGTH: 10
<212> TYPE: PRT
<213> ORGANISM: Artificial Sequence
<220> FEATURE:
<223> OTHER INFORMATION: synthetic construct

<400> SEQUENCE: 78

Gln Glu Tyr Asn Asn Asp Ser Pro Leu Thr
1               5                   10

<210> SEQ ID NO 79
<211> LENGTH: 11
<212> TYPE: PRT
<213> ORGANISM: Artificial Sequence
<220> FEATURE:
<223> OTHER INFORMATION: synthetic construct

<400> SEQUENCE: 79

Arg Ala Ser Gln Ser Ile Ser Ser Trp Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: synthetic construct

<400> SEQUENCE: 80

Lys Ala Ser Gln Leu Glu Ser
1               5

<210> SEQ ID NO 81
<211> LENGTH: 10
<212> TYPE: PRT
<213> ORGANISM: Artificial Sequence
<220> FEATURE:
<223> OTHER INFORMATION: synthetic construct

<400> SEQUENCE: 81

Gln Leu Tyr Asn Val Tyr Ser Pro Leu Thr
1               5                   10

<210> SEQ ID NO 82
<211> LENGTH: 7
<212> TYPE: PRT
<213> ORGANISM: Artificial Sequence
<220> FEATURE:
<223> OTHER INFORMATION: synthetic construct

<400> SEQUENCE: 82

Lys Ala Ser Thr Leu Glu Ser
1               5

<210> SEQ ID NO 83
```

```
<211> LENGTH: 10
<212> TYPE: PRT
<213> ORGANISM: Artificial Sequence
<220> FEATURE:
<223> OTHER INFORMATION: synthetic construct

<400> SEQUENCE: 83

Gln Glu Tyr Asn Asn Asn Ser Pro Leu Thr
1               5                   10

<210> SEQ ID NO 84
<211> LENGTH: 11
<212> TYPE: PRT
<213> ORGANISM: Artificial Sequence
<220> FEATURE:
<223> OTHER INFORMATION: synthetic construct

<400> SEQUENCE: 84

Arg Ala Ser Gln Ser Ile Asp Ser Trp Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: synthetic construct

<400> SEQUENCE: 85

Lys Ala Ser Asn Leu Glu Ser
1               5

<210> SEQ ID NO 86
<211> LENGTH: 8
<212> TYPE: PRT
<213> ORGANISM: Artificial Sequence
<220> FEATURE:
<223> OTHER INFORMATION: synthetic construct

<400> SEQUENCE: 86

Gln Leu Tyr Asn Val His Leu Ile
1               5

<210> SEQ ID NO 87
<211> LENGTH: 11
<212> TYPE: PRT
<213> ORGANISM: Artificial Sequence
<220> FEATURE:
<223> OTHER INFORMATION: synthetic construct

<400> SEQUENCE: 87

Arg Ala Ser Gln Ser Ile Ser Thr Trp Leu Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: synthetic construct

<400> SEQUENCE: 88

Gln Glu Tyr Asn Asn Asp Ser Pro Leu Ile
1               5                   10

<210> SEQ ID NO 89
<211> LENGTH: 11
```

```
<212> TYPE: PRT
<213> ORGANISM: Artificial Sequence
<220> FEATURE:
<223> OTHER INFORMATION: synthetic construct

<400> SEQUENCE: 89

Arg Ala Ser Gln Ser Ile Ser Ser Tyr Leu Ala
1               5                   10

<210> SEQ ID NO 90
<211> LENGTH: 5
<212> TYPE: PRT
<213> ORGANISM: Artificial Sequence
<220> FEATURE:
<223> OTHER INFORMATION: synthetic construct

<400> SEQUENCE: 90

Lys Tyr Ala Ile Asn
1               5

<210> SEQ ID NO 91
<211> LENGTH: 17
<212> TYPE: PRT
<213> ORGANISM: Artificial Sequence
<220> FEATURE:
<223> OTHER INFORMATION: synthetic construct

<400> SEQUENCE: 91

Gly Ile Ile Ala Ile Phe Asn Thr Ala Asn Tyr Ala Gln Lys Phe Gln
1               5                   10                  15

Gly

<210> SEQ ID NO 92
<211> LENGTH: 11
<212> TYPE: PRT
<213> ORGANISM: Artificial Sequence
<220> FEATURE:
<223> OTHER INFORMATION: synthetic construct

<400> SEQUENCE: 92

Gly Met Asn Tyr Tyr Ser Asp Tyr Phe Asp Tyr
1               5                   10

<210> SEQ ID NO 93
<211> LENGTH: 12
<212> TYPE: PRT
<213> ORGANISM: Artificial Sequence
<220> FEATURE:
<223> OTHER INFORMATION: synthetic construct

<400> SEQUENCE: 93

Arg Ala Ser Gln Ser Val Arg Ser Asn Asn Leu Ala
1               5                   10

<210> SEQ ID NO 94
<211> LENGTH: 7
<212> TYPE: PRT
<213> ORGANISM: Artificial Sequence
<220> FEATURE:
<223> OTHER INFORMATION: synthetic construct

<400> SEQUENCE: 94

Gly Ala Ser Ser Arg Ala Thr
1               5

<210> SEQ ID NO 95
```

```
<211> LENGTH: 10
<212> TYPE: PRT
<213> ORGANISM: Artificial Sequence
<220> FEATURE:
<223> OTHER INFORMATION: synthetic construct

<400> SEQUENCE: 95

Gln Gln Tyr Gly Ser Ser Pro Ala Leu Thr
1               5                   10
```